US011629143B2

(12) United States Patent
Flynn et al.

(10) Patent No.: US 11,629,143 B2
(45) Date of Patent: Apr. 18, 2023

(54) HIPK4 INHIBITORS AND USES THEREOF

(71) Applicant: Vibliome Therapeutics, LLC, Bozeman, MT (US)

(72) Inventors: Gary A. Flynn, Bozeman, MT (US); Ashok Bajji, Bozeman, MT (US); Khoi Huynh, Bozeman, MT (US)

(73) Assignee: VIBLIOME THERAPEUTICS, LLC, Bozeman, MT (US)

( * ) Notice: Subject to any disclaimer, the term of this patent is extended or adjusted under 35 U.S.C. 154(b) by 0 days.

(21) Appl. No.: 17/490,654

(22) Filed: Sep. 30, 2021

(65) Prior Publication Data

US 2022/0106303 A1 Apr. 7, 2022

Related U.S. Application Data

(60) Provisional application No. 63/086,250, filed on Oct. 1, 2020.

(51) Int. Cl.
*C07D 413/14* (2006.01)
*C07D 417/12* (2006.01)
*C07D 413/12* (2006.01)

(52) U.S. Cl.
CPC ......... *C07D 413/14* (2013.01); *C07D 413/12* (2013.01); *C07D 417/12* (2013.01); *C07B 2200/05* (2013.01)

(58) Field of Classification Search
CPC ............... C07D 413/14; C07D 413/12; C07D 417/12; C07B 2200/05
USPC ..................................................... 514/210.2
See application file for complete search history.

(56) References Cited

U.S. PATENT DOCUMENTS

| 6,187,797 | B1 | 2/2001 | Pruitt et al. |
| 9,221,805 | B2 | 12/2015 | Flynn |
| 9,833,455 | B2 | 12/2017 | Flynn |
| 2007/0072862 | A1 | 3/2007 | Dimauro et al. |
| 2010/0330069 | A1 | 12/2010 | Wrasidlo et al. |
| 2011/0159111 | A1 | 6/2011 | Curry et al. |
| 2018/0125848 | A1 | 5/2018 | Flynn |

FOREIGN PATENT DOCUMENTS

| WO | 1998/28282 | A2 | 7/1998 |
| WO | 2001/53274 | A1 | 7/2001 |
| WO | 2003/028641 | A2 | 4/2003 |
| WO | 2007/125330 | A1 | 11/2007 |
| WO | 2008/058037 | A1 | 5/2008 |
| WO | 2009/077990 | A1 | 6/2009 |

OTHER PUBLICATIONS

U.S. Appl. No. 14/172,972, filed Feb. 5, 2014, Abandoned.
U.S. Appl. No. 14/173,125, filed Feb. 5, 2014, U.S. Pat. No. 9,221,805, Issued.
U.S. Appl. No. 14/939,886, filed Nov. 12, 2015, U.S. Pat. No. 9,833,455, Issued.
U.S. Appl. No. 15/801,468, filed Nov. 2, 2017, 2018-0125848, Abandoned.
U.S. Appl. No. 16/240,219, filed Jan. 4, 2019, Abandoned.
U.S. Appl. No. 16/554,676, filed Aug. 29, 2019, Abandoned.
U.S. Appl. No. 16/845,119, filed Apr. 10, 2020, Abandoned.
U.S. Appl. No. 17/100,436, filed Nov. 20, 2020, Abandoned.
U.S. Appl. No. 17/366,733, filed Jul. 2, 2021, Pending.
Agid et al., How can drug discovery for psychiatric disorders be improved? Nat Rev Drug Discov. Mar. 2007;6(3):189-201.
Blaquiere et al., Homeodomain-interacting protein kinase promotes tumorigenesis and metastatic cell behavior. Dis Model Mech. Jan. 17, 2018;11(1):dmm031146, 13 pages.
Brinkmann et al., Fingolimod (FTY720): discovery and development of an oral drug to treat multiple sclerosis. Nat Rev Drug Discov. 2010;9(11):883-97.
Brunton et al., Chemotherapy of Neoplastic Diseases. Goodman & Gilman's, The Pharmacological Basis of Therapeutics, 11th Edition. pp. 853-908, (2008).
Buxton, ABC of Dermatology, Fourth Edition. EBSCO Publishing. 28 pages, (2003).
CAS Registry No. 1002046-03-8, dated Feb. 7, 2008.
CAS Registry No. 1061583-38-7, dated Oct. 15, 2008.
CAS Registry No. 1135141-96-6, dated Apr. 16, 2009.
CAS Registry No. 1171529-69-3, dated Aug. 2, 2009.
CAS Registry No. 1181502-59-9, dated Sep. 9, 2009.
CAS Registry No. 1215821-19-4, dated Apr. 2, 2010.
CAS Registry No. 1323344-92-8, dated Aug. 25, 2011.
CAS Registry No. 1323603-46-8, dated Aug. 26, 2011.
CAS Registry No. 956514-87-7, dated Dec. 3, 2007.
CAS Registry No. 956733-18-9, dated Dec. 5, 2007.
CAS Registry No. 957047-35-7, dated Dec. 7, 2007.
CAS Registry No. 958576-36-8, dated Dec. 18, 2007.
Cook et al., Treatment of stroke with a PSD-95 inhibitor in the gyrencephalic primate brain. Nature. Feb. 2, 20129;483(7388):213-7.
Crapster et al., HIPK4 is essential for murine spermiogenesis. Elife. Mar. 12, 2020;9:e50209, 27 pages.
D'Ambrosio et al., Chemokine receptors in inflammation: an overview. J Immunol Methods. Feb. 2003;273(1-2):3-13. Dietrich et al., Application of a novel [3+2] cycloaddition reaction to prepare substituted imidazoles and their use in the design of potent DFG-out allosteric B-Raf inhibitors Bioorganic & Medicinal Chemistry. 2010;18:292-304.
Ermolat'ev et al., Microwave-assisted synthesis of substituted 2-amino-1H-imidazoles from imidazo[1,2-alpha] pyrimidines. Tetrahedron Letters. 2009;50:5218-20.
Fevig et al., Synthesis and SAR of benzamidine factor Xa inhibitors containing a vicinally-substituted heterocyclic core. Bioorg Med Chem Lett. Mar. 12, 2001;11 (5):641-5.
Fox et al., Dermatological Pharmacology. Goodman & Gilman's The Pharmacological Basis of Therapeutics. 11th Edition. Chapter 62, pp. 1679-1705, (2006).

(Continued)

*Primary Examiner* — Kahsay Habte
(74) *Attorney, Agent, or Firm* — McCarter & English, LLP; Jonathan M. Sparks; Michael J. DeGrazia

(57) ABSTRACT

Provided herein are protein kinase inhibitors, which, in one aspect are selective inhibitors of HipK4. Pharmaceutical compositions and medical uses for the disclosed inhibitors are also provided.

4 Claims, No Drawings

(56) References Cited

OTHER PUBLICATIONS

Ha et al., Risk of arterial thrombotic events in inflammatory bowel disease. Am J Gastroenterol. Jun. 2009;104(6):1445-51.

He et al., Characterization of Human Homeodomain-interacting Protein Kinase 4 (HIPK4) as a Unique Member of the HIPK Family. Mol Cell Pharmacol. 2010;2(2):61-68.

Henderer et al., Ocular Pharmacology. Goodman & Gilman's, The Pharmacological Basis of Therapeutics, eleventh edition. McGraw-Hill, New York. Chapter 63, pp. 1707-1737, (2006).

Judge et al., Potassium channel blockers in multiple sclerosis: neuronal Kv channels and effects of symptomatic treatment. Pharmacol Ther. Jul. 2006;111(1):224-59.

Kim et al., Homeodomain-interacting protein kinases, a novel family of co-repressors for homeodomain transcription Factors. J Biol Chem. Oct. 2, 1998;273(40):25875-9.

Koelink et al., Targeting chemokine receptors in chronic inflammatory diseases: an extensive review. Pharmacol Ther. Jan. 2012;133(1):1-18.

Kuster, Kinase Inhibitors, Methods and Protocols. Humana Press. vol. 795, chapters 1 and 2, pp. 1-44, (2012).

Müller et al., Antiviral Strategies, Handbook of Experimental Pharmacology. Springer-Veriag, Berlin, pp. 1-24, (2009).

Steenackers et al., Structure-activity relationship of 4(5)-aryl-2-amino-1H-imidazoles, N1-substituted 2-aminoimidazoles and imidazo[1,2-a]pyrimidinium salts as inhibitors of biofilm formation by *Salmonella typhimurium* and Pseudomonas aeruginosa. J Med Chem. Jan. 27, 2011;54(2):472-84.

Sutherland et al., Management of chronic obstructive pulmonary disease. N Engl J Med. Jun. 24, 2004;350(26):2689-97.

Turko et al., Protein nitration in cardiovascular diseases. Pharmacol Rev. Dec. 2002,54(4):619-34.

Yoon et al., Impact of fluoroquinolones on the diagnosis of pulmonary tuberculosis initially treated as bacterial pneumonia. Int J Tuberc Lung Dis Nov. 2005;9(11):1215-9.

Zakrzewska et al., Trigeminal neuralgia: the diagnosis and management of this excruciating and pooriy understood facial pain. Postgrad Med J. Jun. 2011;87(1028):410-6.

Zuccotto et al., Through the "Gatekeeper Door": Exploiting the Active Kinase Conformation. J Med Chem. Apr. 8, 2010;53(7):2681-94.

HIPK4 INHIBITORS AND USES THEREOF

RELATED APPLICATIONS

This application claims the benefit of U.S. Provisional Application No. 63/086,250, filed Oct. 1, 2020, the entire contents of which are expressly incorporated herein by reference.

BACKGROUND

The homeodomain-interacting protein kinase (HipK) family of proteins are implicated in the regulation of numerous signaling pathways required for the development of healthy tissues as well as in the development and progression of multiple diseases. See e.g., Disease Models & Mechanisms 2018 11: dmm031146 doi: 10.1242/dmm.031146 Published 17 Jan. 2018. To date, 4 isoforms are known: HipK1, HipK2, HipK3 and HipK4 (Kim Choi et al. 1998, J Biol Chem, 273(40): 25875-9). Less is known to date about HipK4, although it has recently gained attention for its role in spermiogenesis (Elife. 2020; 9:e50209. Published 2020 Mar. 12. doi:10.7554/eLife.50209) as well as for the treatment of certain cancers (Mol Cell Pharmacol. 2010; 2(2):61-68).

Given its therapeutic benefits, new chemical modulators HipK4 are needed.

SUMMARY

Provided herein are protein kinase inhibitors, which, in one aspect are selective inhibitors of HipK4.

Also provided are pharmaceutically acceptable compositions comprising the disclosed protein kinase inhibitors.

Further proved is the use of one or more protein kinase inhibitors, or a pharmaceutically acceptable composition thereof, for the treatment of a disease or disorder relate to the inhibition of HipK4.

DETAILED DESCRIPTION

In one aspect, provided are compound having the structural formula selected from:

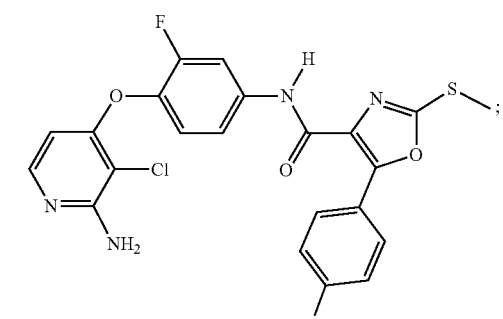

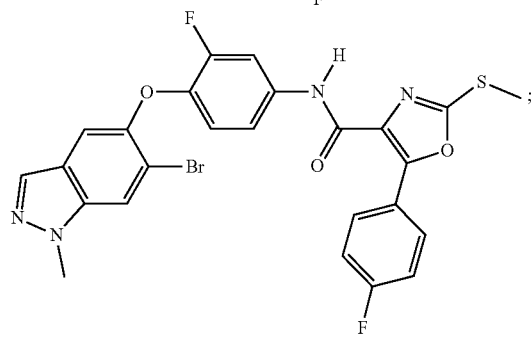

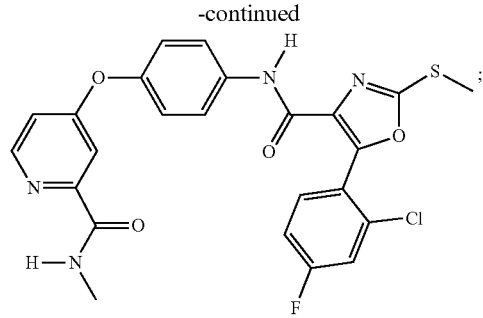

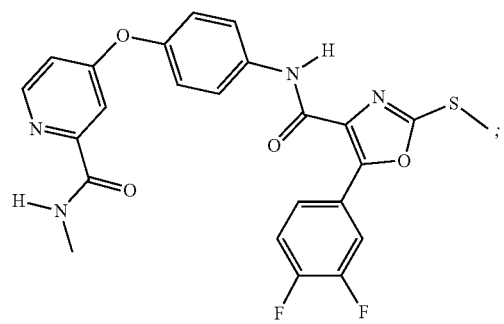

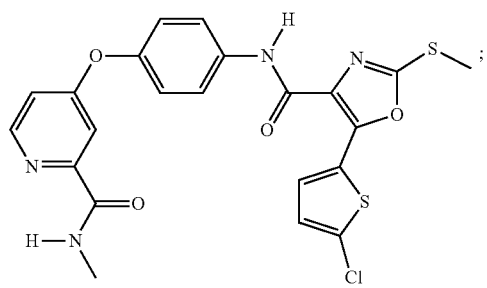

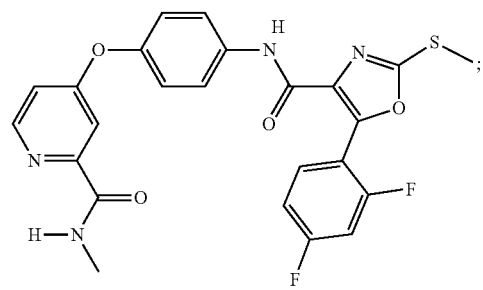

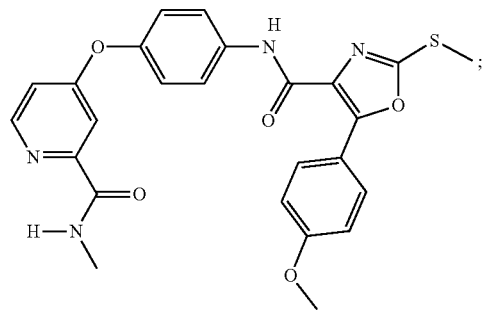

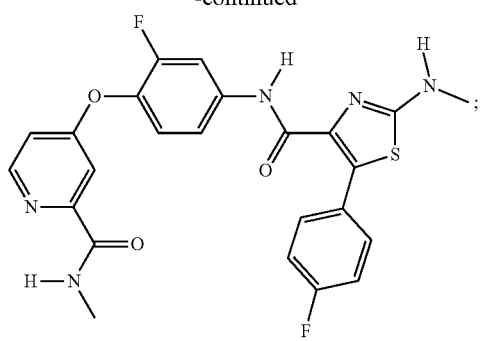
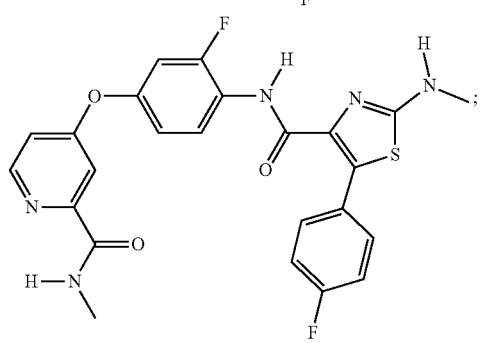
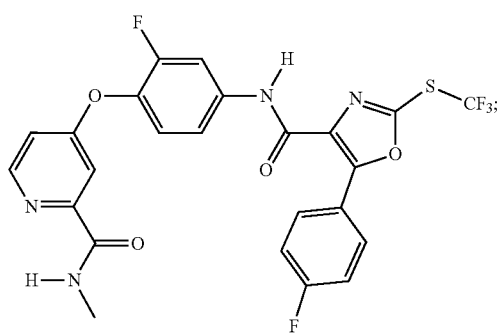
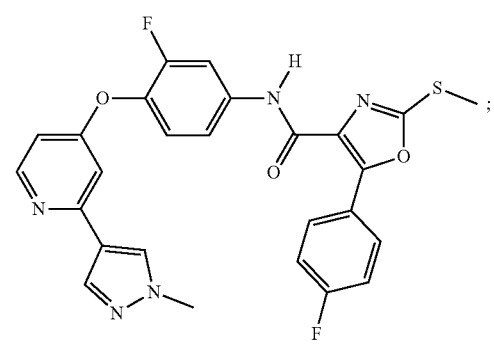
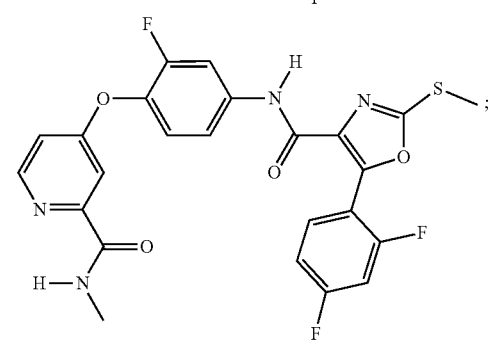
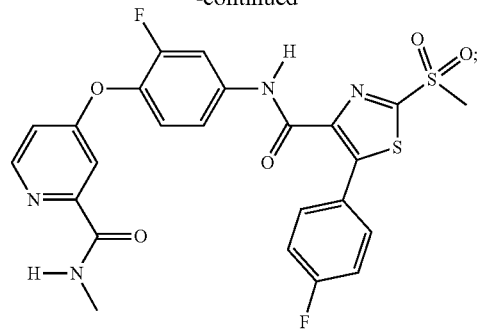
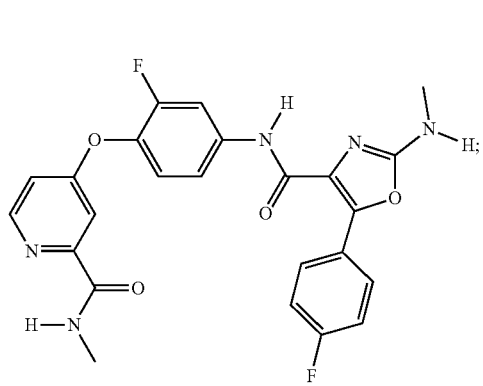
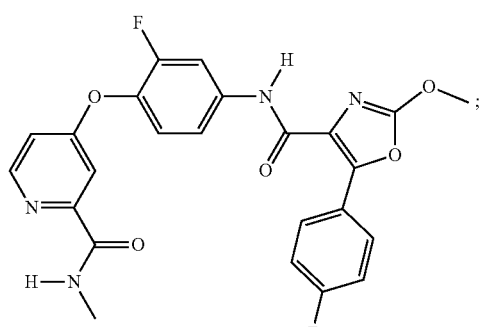
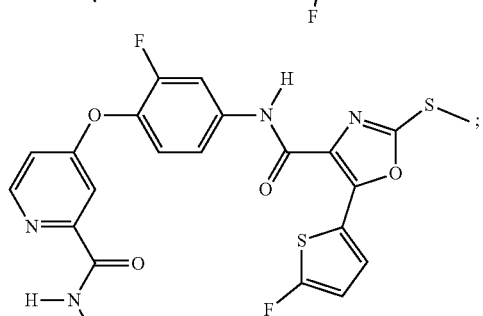
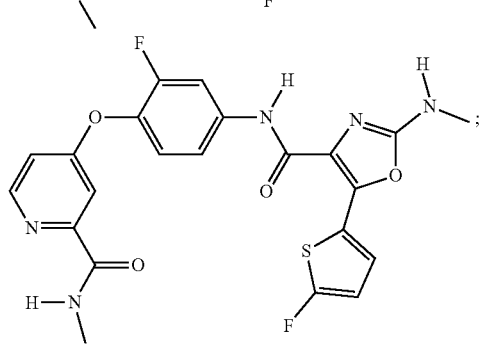

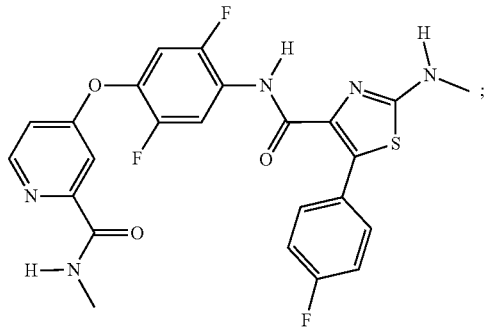
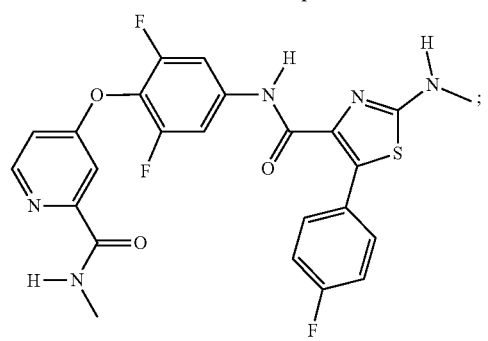
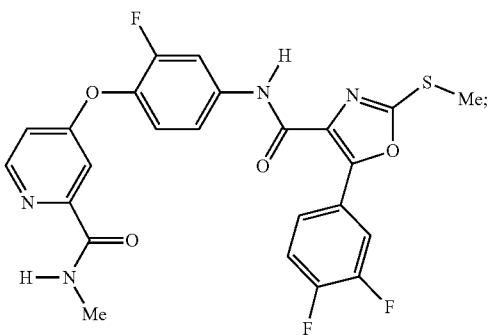
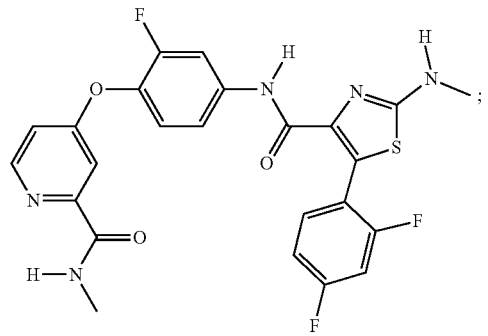
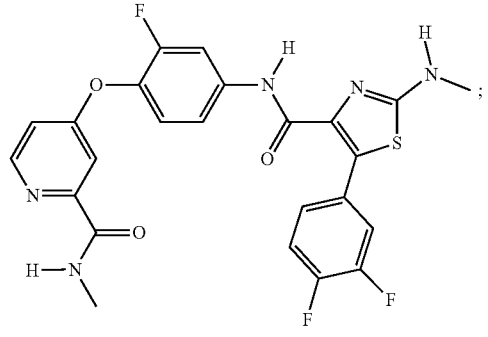
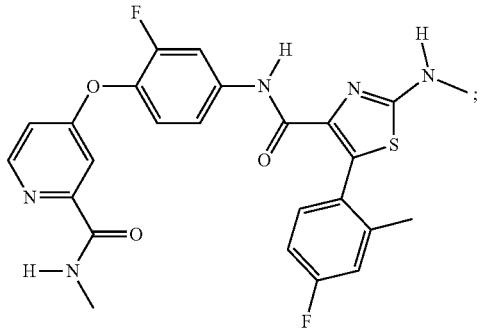
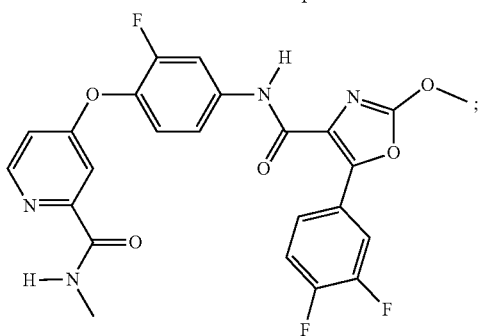
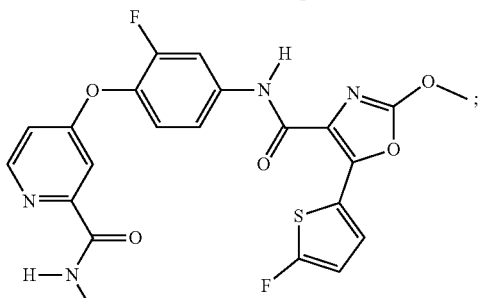
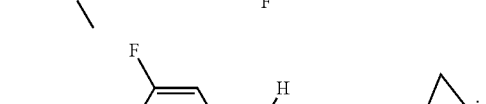
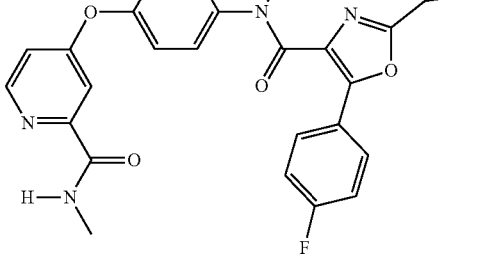
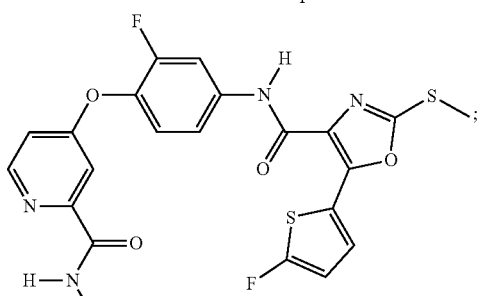

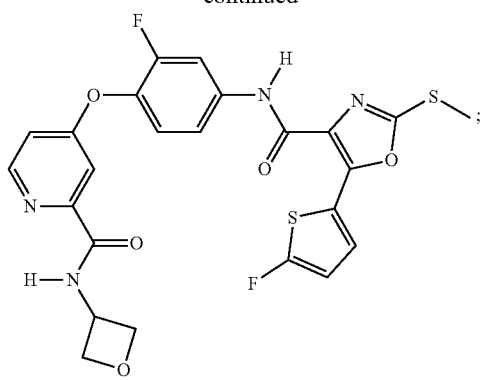
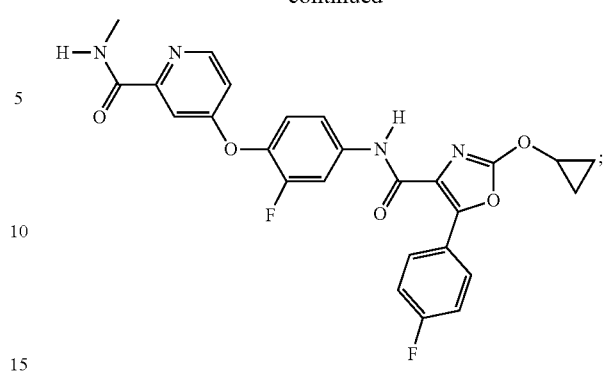
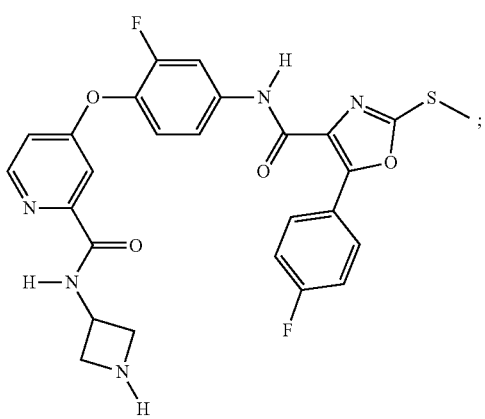
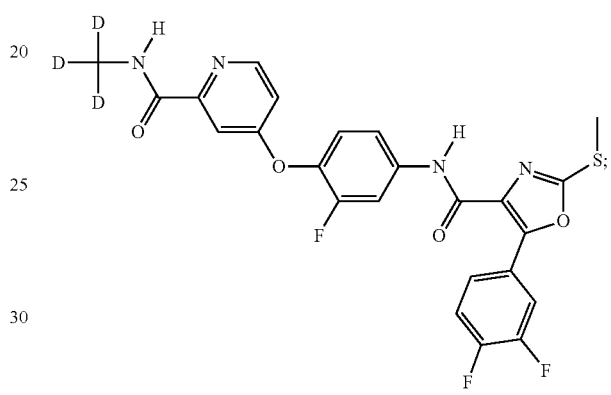
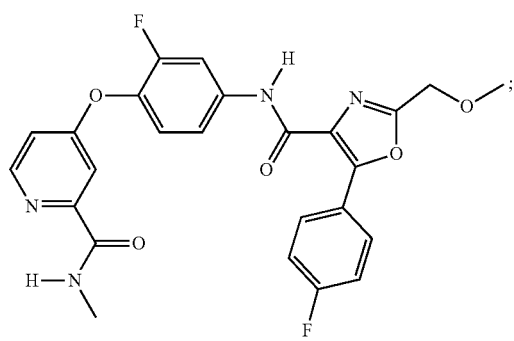
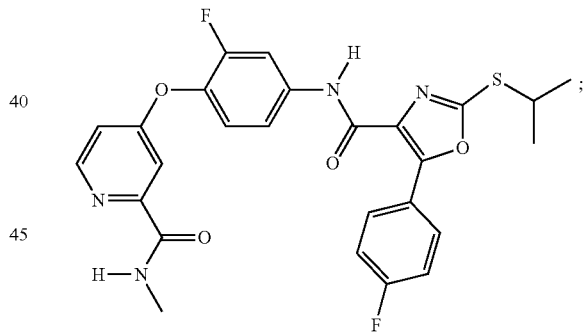
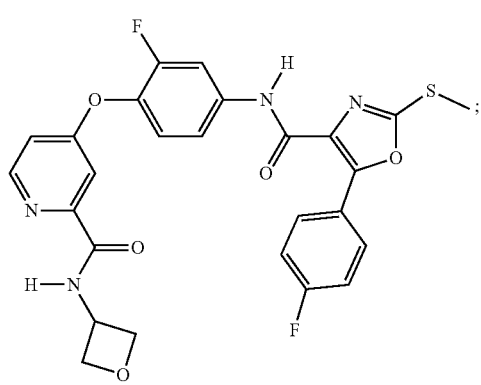
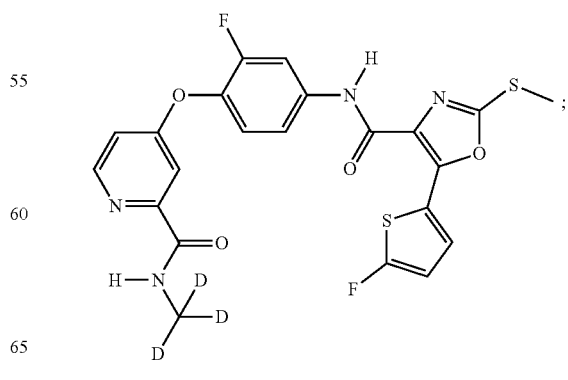

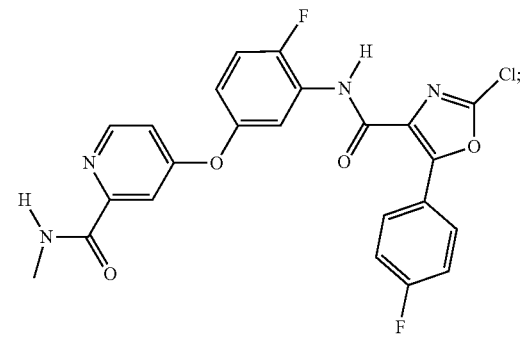 [SMILES: CNC(=O)c1cc(Oc2ccc(F)c(NC(=O)c3nc(Cl)oc3-c3ccc(F)cc3)c2)ccn1]

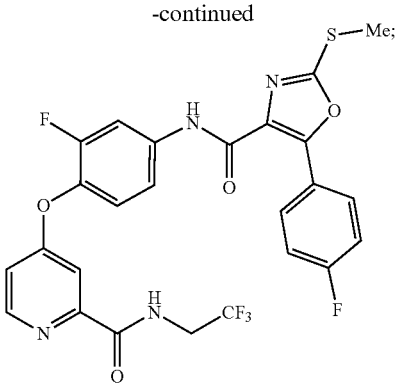

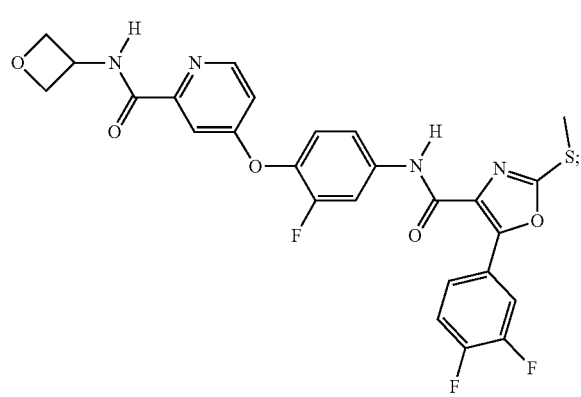

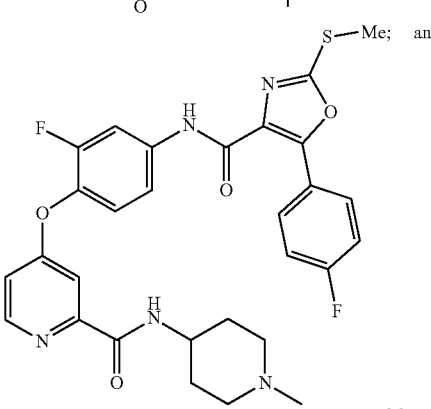

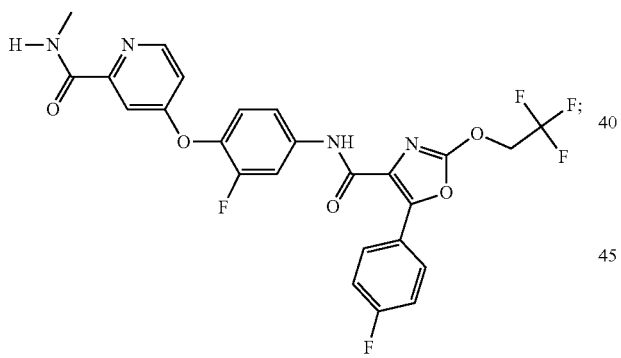

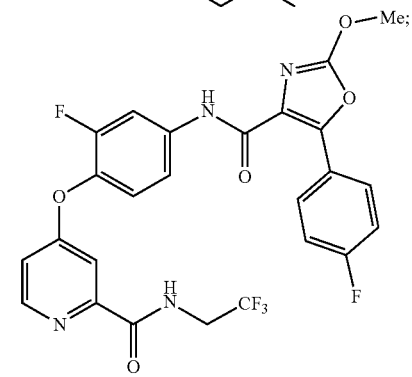

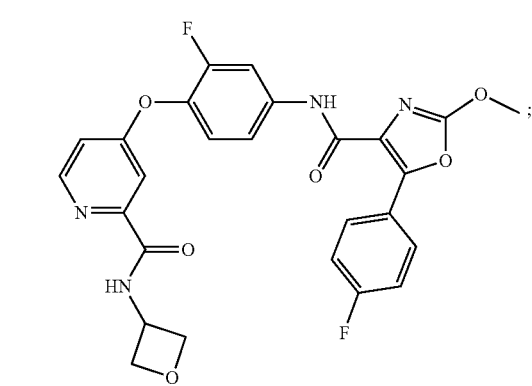

or a pharmaceutically acceptable salt thereof of any of the foregoing.

The terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

The terms "treatment," "treat," and "treating" refer to reversing, alleviating, delaying the onset of, or inhibiting the progress of a disease or disorder, or one or more symptoms thereof, as described herein. In some aspects, treatment may be administered after one or more symptoms have developed, i.e., therapeutic treatment. In other aspects, treatment may be administered in the absence of symptoms. For example, treatment may be administered to a susceptible individual prior to the onset of symptoms (e.g., in light of a history of symptoms and/or in light of exposure to a particular organism, or other susceptibility factors), i.e., prophylactic treatment. Treatment may also be continued after symptoms have resolved, for example to delay their recurrence.

The term "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

For use in medicines, the salts of the compounds described herein refer to non-toxic "pharmaceutically acceptable salts." Pharmaceutically acceptable salt forms include pharmaceutically acceptable acidic/anionic or basic/cationic salts. Suitable pharmaceutically acceptable acid addition salts of the compounds described herein include e.g., salts of inorganic acids (such as hydrochloric acid, hydrobromic, phosphoric, nitric, and sulfuric acids) and of organic acids (such as, acetic acid, benzenesulfonic, benzoic, methanesulfonic, and p-toluenesulfonic acids). Compounds of the present teachings with acidic groups such as carboxylic acids can form pharmaceutically acceptable salts with pharmaceutically acceptable base(s). Suitable pharmaceutically acceptable basic salts include e.g., ammonium salts, alkali metal salts (such as sodium and potassium salts) and alkaline earth metal salts (such as magnesium and calcium salts). Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, benzoates and salts with amino acids such as glutamic acid.

The term "effective amount" or "therapeutically effective amount" refers to an amount of a compound described herein that will elicit a desired or beneficial biological or medical response of a subject e.g., a dosage of between 0.01-100 mg/kg body weight/day.

Compounds and compositions described herein are generally useful for inhibiting the activity of one or more protein kinases. In one aspect, the compounds and pharmaceutical compositions described herein inhibit the activity HipK4.

In some aspects, compounds and pharmaceutical compositions described herein are useful in treating a disease or disorder associated with HipK4 function. Thus, provided herein are methods of treating a disease or disorder associated with HipK4 function, comprising administering to a subject in need thereof, a therapeutically effective amount of a compound described herein, or a pharmaceutically acceptable salt thereof, or a pharmaceutical composition comprising a disclosed compound or pharmaceutically acceptable salt thereof. Also provided is the use of a compound described herein, or a pharmaceutically acceptable salt thereof, or a pharmaceutical composition comprising a disclosed compound or pharmaceutically acceptable salt thereof, for the manufacture of a medicament for treating a disease or disorder associated with HipK4 function. Also provided is a compound described herein, or a pharmaceutically acceptable salt thereof, or a pharmaceutical composition comprising a disclosed compound or pharmaceutically acceptable salt thereof, for use in treating a disease or disorder associated with HipK4.

In some aspects, the compounds and pharmaceutical compositions described herein are useful in treating cancer.

In some aspects, the cancer treated by the compounds and pharmaceutical compositions described herein is selected from prostate cancers, lung cancers (e.g., adenosquamous lung carcinoma and squamous cell carcinoma), pancreatic cancers, bladder cancers, colon cancers, diffuse large B-cell lymphomas, rectal cancers, melanomas, stomach cancers, esophageal cancers, and uterine cancers.

In some aspects, the compounds and pharmaceutical compositions described herein are useful for contraception.

In certain aspects, a pharmaceutical composition described herein is formulated for administration to a patient in need of such composition. Pharmaceutical compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions are administered orally, intraperitoneally or intravenously. Sterile injectable forms of the pharmaceutical compositions described herein may be aqueous or oleaginous suspension. These suspensions may be formulated according to techniques known in the art using suitable dispersing or wetting agents and suspending agents.

In some aspects, the pharmaceutical compositions are administered orally.

A specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound described herein in the composition will also depend upon the particular compound in the pharmaceutical composition.

Exemplification

Representative examples of the disclosed compounds are illustrated in the following non-limiting methods, schemes, and examples.

Synthetic Methods

Synthesis of 4-(4-amino-2-fluoro-phenoxy)-N-(2,2,2-trifluoroethyl)pyridine-2-carboxamide intermediate

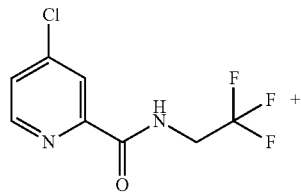

+

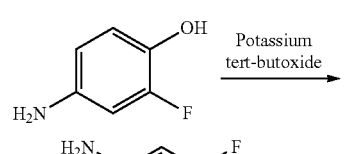

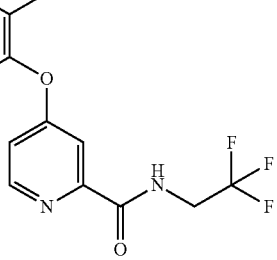

To a mixture of 4-Amino-2-fluorophenol (1.33 g, 10.5 mmol, 0.919 eq) in DMSO (11.42 mL, 1.0000 M) was added Potassium tert-butoxide (2.49 g, 22.2 mmol, 1.94 eq). The reaction mixture was stirred for 2 h at 23° C., then 4-chloro-N-(2,2,2-trifluoroethyl)pyridine-2-carboxamide (2.72 g, 11.4 mmol, 1.00 eq) were added. The solution was stirred at 80° C. for 23 h. The solution was diluted with EtOAc (40 mL) and washed with H$_2$O (2×20 mL), and brine (20 mL), and dried over MgSO$_4$. The solvent was removed by rotary evaporation, and the residue was purified by flash column chromatography (1:2 EtOAc/Hex) to afford 4-(4-amino-2-fluoro-phenoxy)-N-(2,2,2-trifluoroethyl)pyridine-2-carboxamide (3.01 g, 8.13 mmol, 71.22% yield). ESI-MS m/z calc. 329, found 330 (M+1)$^+$; Retention time: 6.01 minutes.

Synthesis of 5-(4-fluorophenyl)-N-[3-fluoro-4-[[2-(2,2,2-trifluoroethylcarbamoyl)-4-pyridyl]oxy]phenyl]-2-methylsulfanyl-oxazole-4-carboxamide [Example 51]

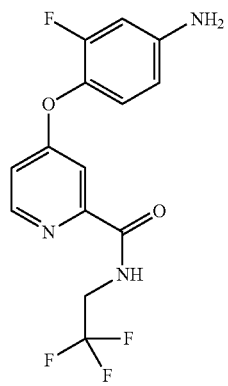

+

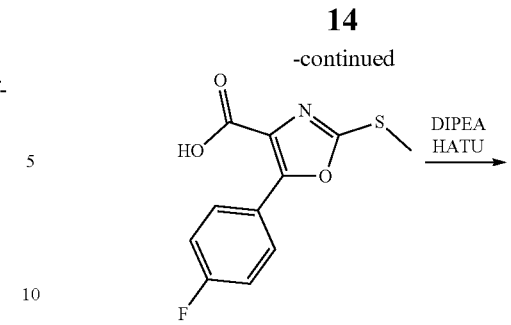

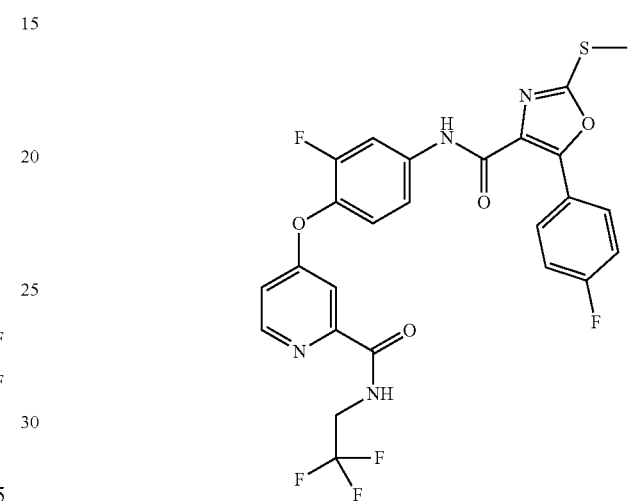

HATU [Hexafluorophosphate Azabenzotriazole Tetramethyl Uronium] (647 mg, 1.70 mmol, 2.00 eq) was added to a solution of 4-(4-amino-2-fluorophenoxy)-N-(2,2,2-trifluoroethyl)picolinamide (280 mg, 0.850 mmol, 1.00 eq), 5-(4-fluorophenyl)-2-(methylthio)oxazole-4-carboxylic acid (263 mg, 1.04 mmol, 1.22 eq) and DIPEA [N,N-diisopropylethyl amine] (0.42 mL, 2.55 mmol, 3.00 eq). The reaction was stirred for 2 hours, after which it was quenched by adding water (25 ml) and the precipitate obtained was filtered. The precipitate was then purified by flash column chromatography (dry loaded, 24 g column) eluting 50-75% Ethyl acetate in hexanes over 15 min. The desired fractions were concentrated to dryness in vacuo to get a foamy solid. The solid was triturated with ether and methanol to get 5-(4-fluorophenyl)-N-[3-fluoro-4-[[2-(2,2,2-trifluoroethylcarbamoyl)-4-pyridyl]oxy]phenyl]-2-methylsulfanyl-oxazole-4-carboxamide (226 mg, 0.396 mmol, 46.51% yield) as a white solid.

$^1$H NMR (500 MHz, DMSO-d6) δ 10.48 (s, 1H), 9.35 (t, J=6.7, 6.7 Hz, 1H), 8.59 (d, J=5.6 Hz, 1H), 8.25-8.17 (m, 2H), 8.03 (dd, J=13.1, 2.4 Hz, 1H), 7.80-7.74 (m, 1H), 7.47-7.40 (m, 2H), 7.40-7.32 (m, 2H), 7.27 (dd, J=5.6, 2.6 Hz, 1H), 4.04 (qd, J=9.5, 9.5, 9.5, 6.9 Hz, 2H), 2.81 (s, 3H). ESI-MS m/z calc. 564.4, found 565.3 (M+1)$^+$; Retention time: 3.37 minutes.

The compounds in Table 1 were prepared using similar procedures to those described for Compound 51 using the appropriate starting materials.

TABLE 1

| Compound Nos. | Structure | ¹H-NMR | Mass Spec. (MZ) |
|---|---|---|---|
| 1 | 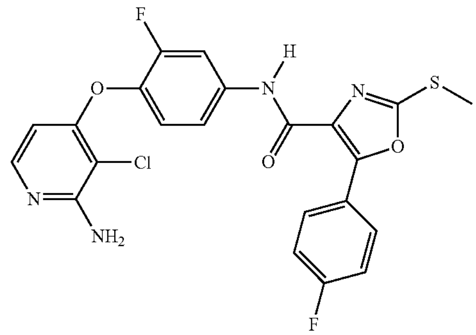 [SMILES: CSc1nc(C(=O)Nc2ccc(Oc3ccnc(N)c3Cl)c(F)c2)c(-c2ccc(F)cc2)o1] | | 489 |
| 2 | 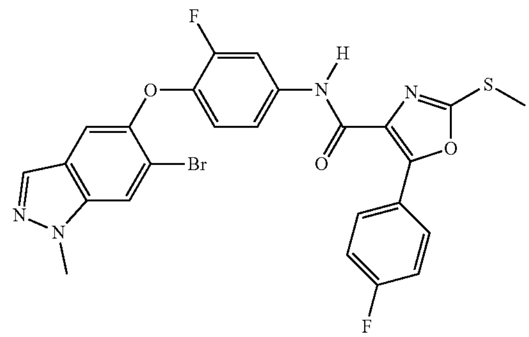 [SMILES: CSc1nc(C(=O)Nc2ccc(Oc3cc4cnn(C)c4cc3Br)c(F)c2)c(-c2ccc(F)cc2)o1] | | 572.8 |
| 3 | 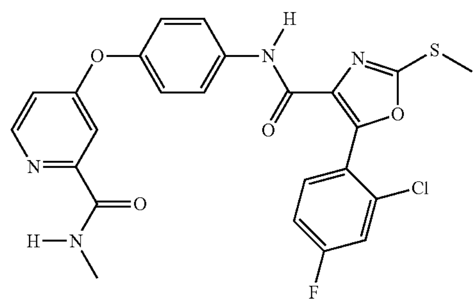 [SMILES: CNC(=O)c1cc(Oc2ccc(NC(=O)c3nc(SC)oc3-c3ccc(F)cc3Cl)cc2)ccn1] | | 513 |
| 4 | 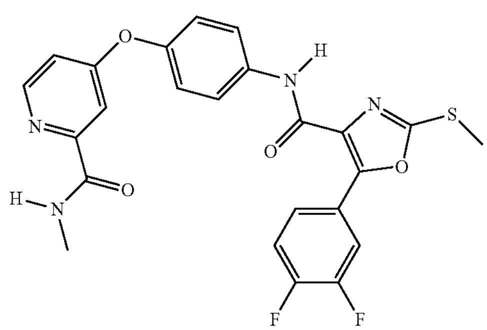 [SMILES: CNC(=O)c1cc(Oc2ccc(NC(=O)c3nc(SC)oc3-c3ccc(F)c(F)c3)cc2)ccn1] | | 497 |
| 5 | 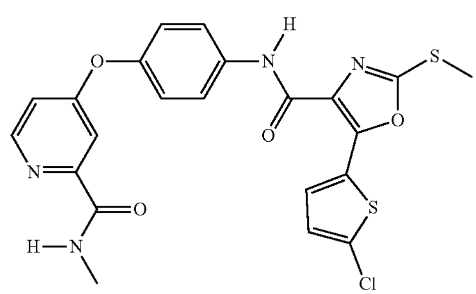 [SMILES: CNC(=O)c1cc(Oc2ccc(NC(=O)c3nc(SC)oc3-c3ccc(Cl)s3)cc2)ccn1] | | 501.2 |

TABLE 1-continued

| Compound Nos. | Structure | $^1$H-NMR | Mass Spec. (MZ) |
|---|---|---|---|
| 6 | 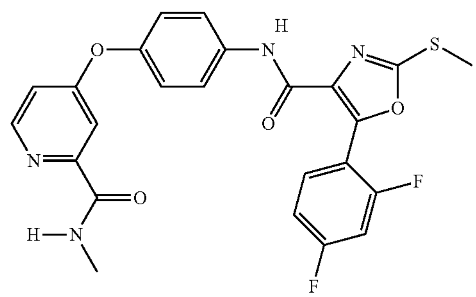 | | 497.5 |
| 7 | 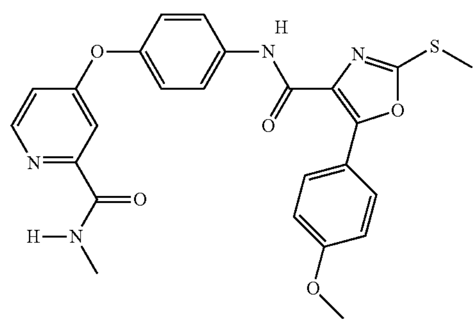 | | 491.2 |
| 8 | 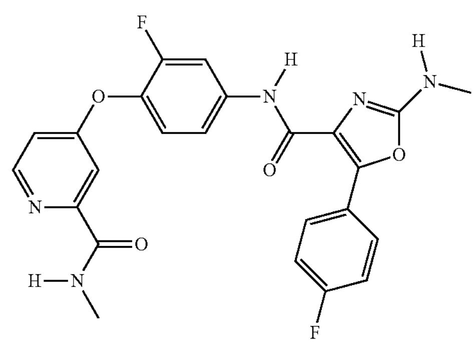 [SMILES: CNC(=O)c1cc(Oc2ccc(NC(=O)c3nc(NC)oc3-c3ccc(F)cc3)cc2F)ccn1] | | 496.1 |
| 9 | 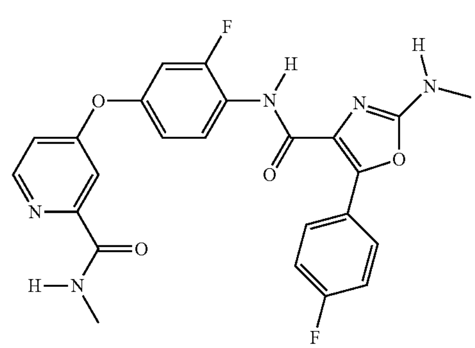 [SMILES: CNC(=O)c1cc(Oc2ccc(NC(=O)c3nc(NC)oc3-c3ccc(F)cc3)c(F)c2)ccn1] | | 248.7 |

TABLE 1-continued

| Compound Nos. | Structure | ¹H-NMR | Mass Spec. (MZ) |
|---|---|---|---|
| 10 | 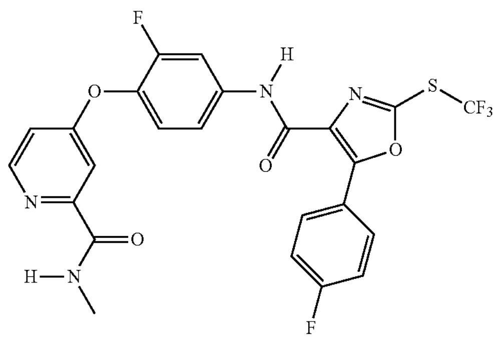 [SMILES: CNC(=O)c1cc(Oc2ccc(NC(=O)c3nc(SC(F)(F)F)oc3-c3ccc(F)cc3)cc2F)ccn1] | | 467 |
| 11 | 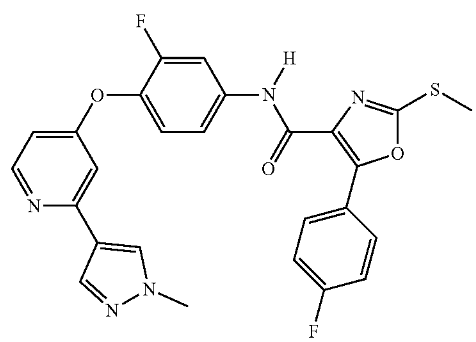 [SMILES: CSc1nc(C(=O)Nc2ccc(Oc3ccnc(-c4cnn(C)c4)c3)c(F)c2)c(-c2ccc(F)cc2)o1] | | 520.1 |
| 12 | 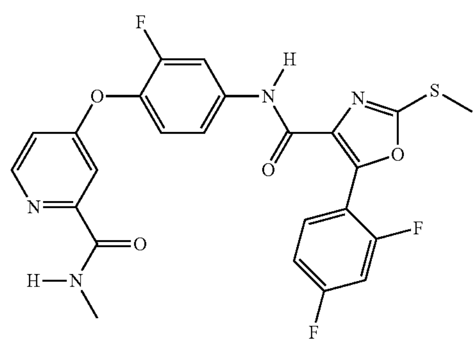 [SMILES: CNC(=O)c1cc(Oc2ccc(NC(=O)c3nc(SC)oc3-c3ccc(F)cc3F)cc2F)ccn1] | | 515.1 |
| 13 | 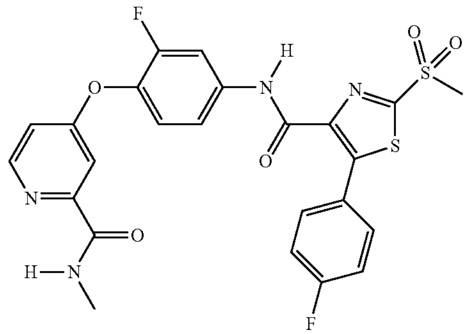 [SMILES: CNC(=O)c1cc(Oc2ccc(NC(=O)c3nc(S(C)(=O)=O)sc3-c3ccc(F)cc3)cc2F)ccn1] | | 545.1 |

TABLE 1-continued
| Compound Nos. | Structure | ¹H-NMR | Mass Spec. (MZ) |
|---|---|---|---|
| 14 | 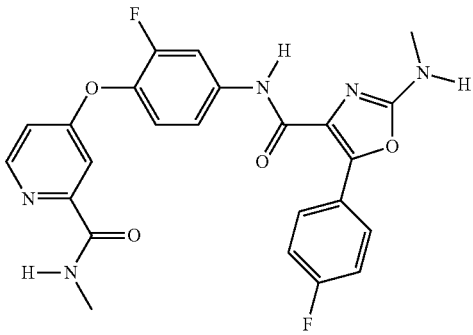 [SMILES: CNC(=O)c1cc(Oc2ccc(NC(=O)c3nc(NC)oc3-c3ccc(F)cc3)cc2F)ccn1] | | 480.1 |
| 15 | 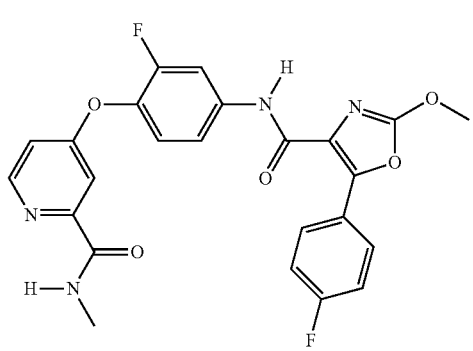 [SMILES: CNC(=O)c1cc(Oc2ccc(NC(=O)c3nc(OC)oc3-c3ccc(F)cc3)cc2F)ccn1] | | 481.1 |
| 16 | 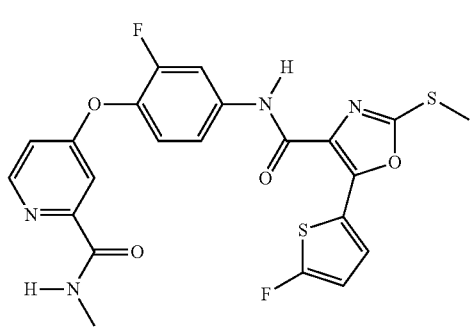 [SMILES: CNC(=O)c1cc(Oc2ccc(NC(=O)c3nc(SC)oc3-c3ccc(F)s3)cc2F)ccn1] | | 503.1 |
| 17 | 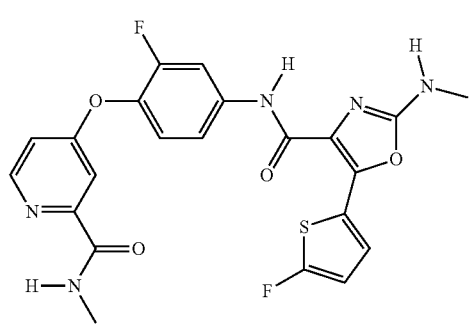 [SMILES: CNC(=O)c1cc(Oc2ccc(NC(=O)c3nc(NC)oc3-c3ccc(F)s3)cc2F)ccn1] | | 486.1 |

TABLE 1-continued

| Compound Nos. | Structure | ¹H-NMR | Mass Spec. (MZ) |
|---|---|---|---|
| 18 | 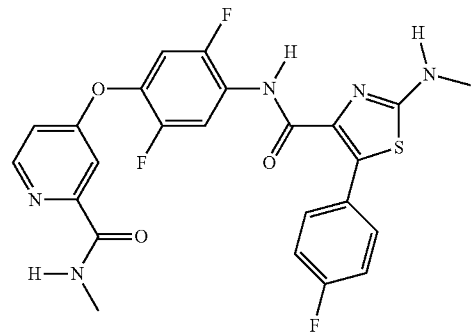 [SMILES: CNC(=O)c1cc(Oc2cc(F)c(NC(=O)c3nc(NC)sc3-c3ccc(F)cc3)cc2F)ccn1] | | 535.0 |
| 19 | 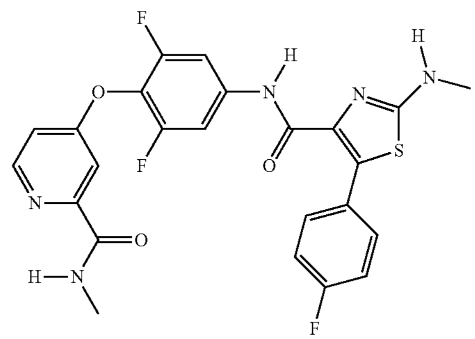 [SMILES: CNC(=O)c1cc(Oc2c(F)cc(NC(=O)c3nc(NC)sc3-c3ccc(F)cc3)cc2F)ccn1] | | 514.2 |
| 20 | 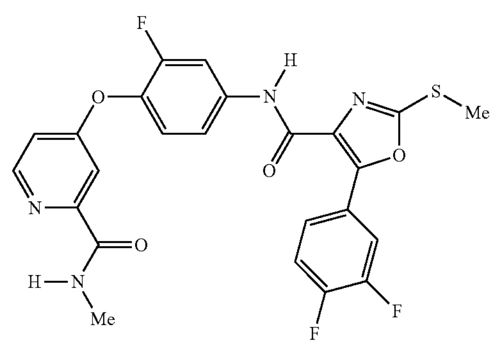 [SMILES: CNC(=O)c1cc(Oc2ccc(NC(=O)c3nc(SC)oc3-c3ccc(F)c(F)c3)cc2F)ccn1] | | 415.1 |
| 21 | 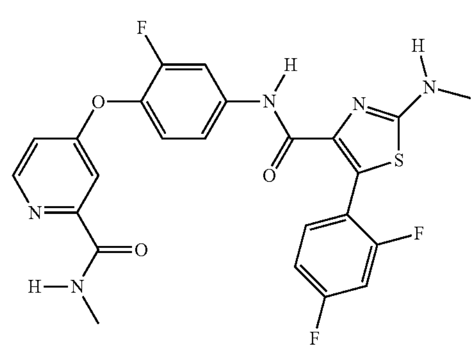 [SMILES: CNC(=O)c1cc(Oc2ccc(NC(=O)c3nc(NC)sc3-c3ccc(F)cc3F)cc2F)ccn1] | | 514.3 |

TABLE 1-continued

| Compound Nos. | Structure | ¹H-NMR | Mass Spec. (MZ) |
|---|---|---|---|
| 22 | 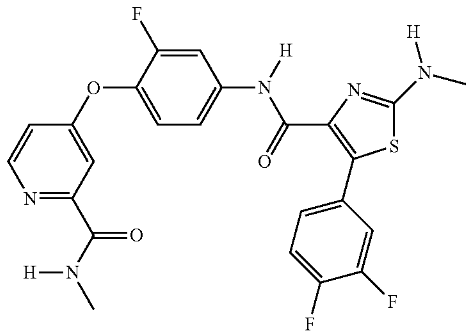 [SMILES: CNC(=O)c1cc(Oc2ccc(NC(=O)c3nc(NC)sc3-c3ccc(F)c(F)c3)cc2F)ccn1] | | 547.1 |
| 23 | 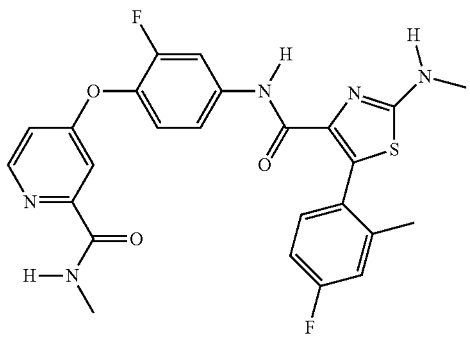 [SMILES: CNC(=O)c1cc(Oc2ccc(NC(=O)c3nc(NC)sc3-c3ccc(F)cc3C)cc2F)ccn1] | | 510.2 |
| 24 | 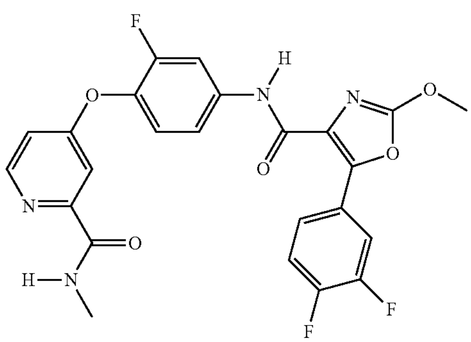 [SMILES: CNC(=O)c1cc(Oc2ccc(NC(=O)c3nc(OC)oc3-c3ccc(F)c(F)c3)cc2F)ccn1] | | 499.2 |
| 25 | 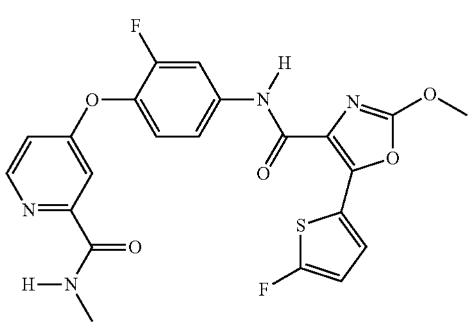 [SMILES: CNC(=O)c1cc(Oc2ccc(NC(=O)c3nc(OC)oc3-c3ccc(F)s3)cc2F)ccn1] | | 487 |

TABLE 1-continued
| Compound Nos. | Structure | ¹H-NMR | Mass Spec. (MZ) |
|---|---|---|---|
| 26 | 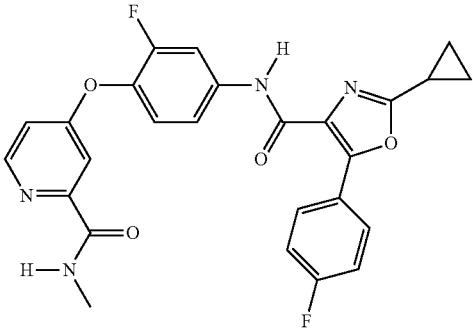 [SMILES: CNC(=O)c1cc(Oc2ccc(NC(=O)c3nc(C4CC4)oc3-c3ccc(F)cc3)cc2F)ccn1] | | 491.1 |
| 27 | 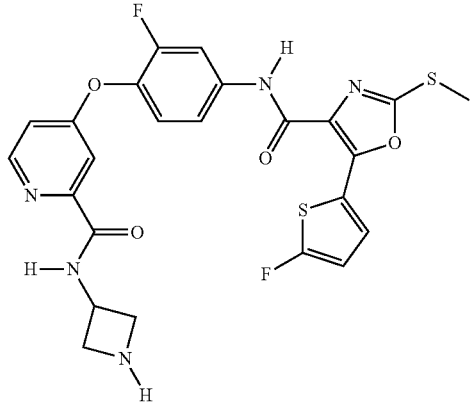 [SMILES: CSc1nc(C(=O)Nc2ccc(Oc3ccnc(C(=O)NC4CNC4)c3)c(F)c2)c(-c2ccc(F)s2)o1] | | 544.1 |
| 28 | 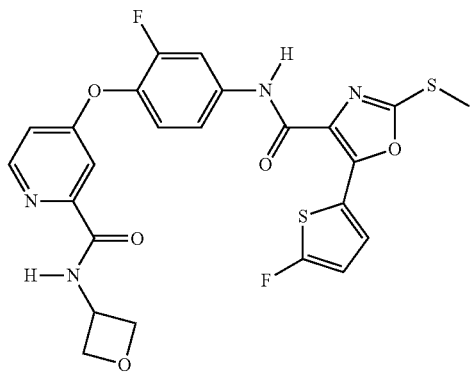 [SMILES: CSc1nc(C(=O)Nc2ccc(Oc3ccnc(C(=O)NC4COC4)c3)c(F)c2)c(-c2ccc(F)s2)o1] | | 545.2 |
| 29 | 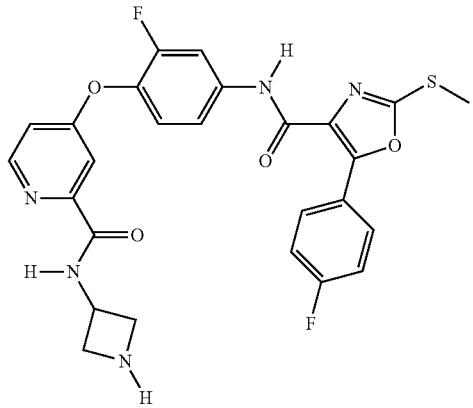 [SMILES: CSc1nc(C(=O)Nc2ccc(Oc3ccnc(C(=O)NC4CNC4)c3)c(F)c2)c(-c2ccc(F)cc2)o1] | | 538.1 |

TABLE 1-continued

| Compound Nos. | Structure | ¹H-NMR | Mass Spec. (MZ) |
|---|---|---|---|
| 30 | 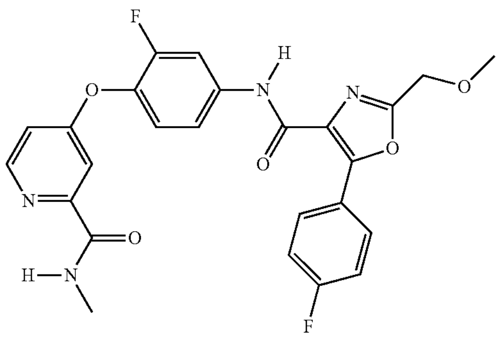 [SMILES: CNC(=O)c1cc(Oc2ccc(NC(=O)c3nc(COC)oc3-c3ccc(F)cc3)cc2F)ccn1] | | 495.1 |
| 31 | 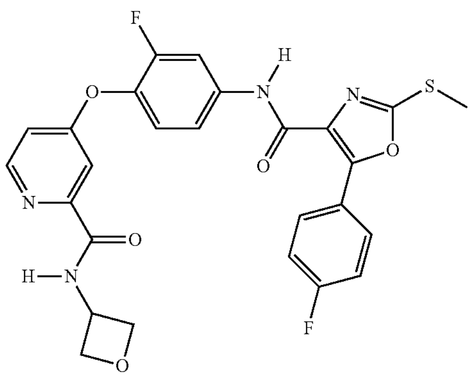 [SMILES: CSc1nc(C(=O)Nc2ccc(Oc3ccnc(C(=O)NC4COC4)c3)c(F)c2)c(-c2ccc(F)cc2)o1] | | 539.1 |
| 32 | 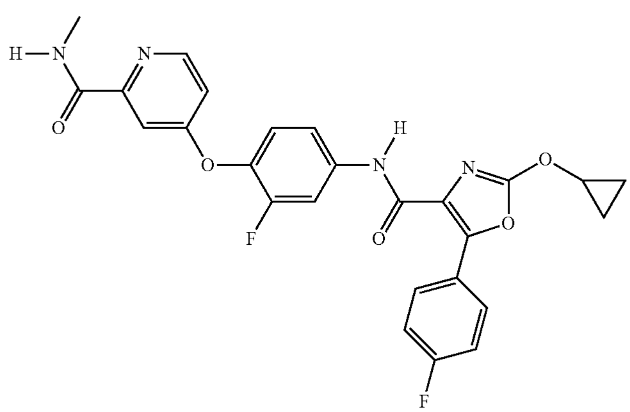 [SMILES: CNC(=O)c1cc(Oc2ccc(NC(=O)c3nc(OC4CC4)oc3-c3ccc(F)cc3)cc2F)ccn1] | | 507.1 |
| 33 | 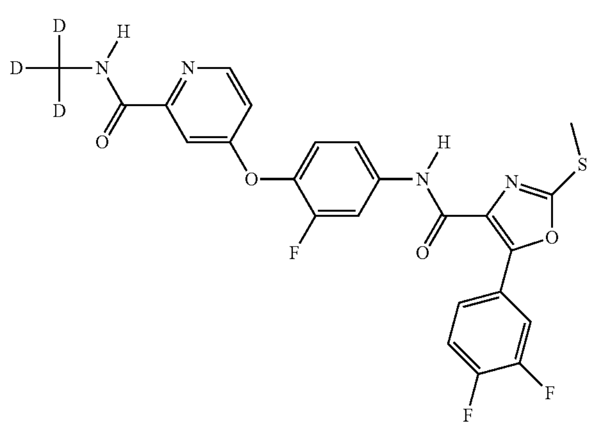 [SMILES: [2H]C([2H])([2H])NC(=O)c1cc(Oc2ccc(NC(=O)c3nc(SC)oc3-c3ccc(F)c(F)c3)cc2F)ccn1] | | 518.1 |

TABLE 1-continued

| Compound Nos. | Structure | ¹H-NMR | Mass Spec. (MZ) |
|---|---|---|---|
| 34 | 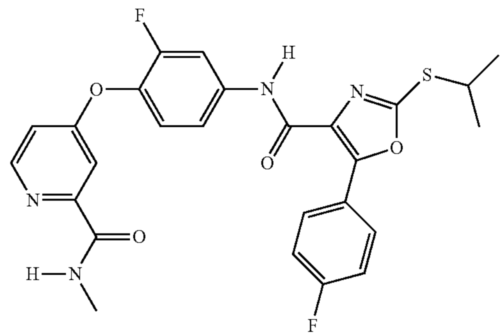 [SMILES: CNC(=O)c1cc(Oc2ccc(NC(=O)c3nc(SC(C)C)oc3-c3ccc(F)cc3)cc2F)ccn1] | | 525.1 |
| 35 | 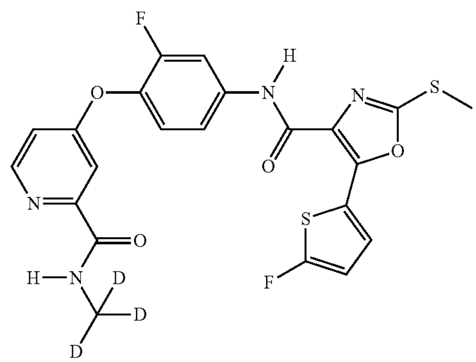 [SMILES: [2H]C([2H])([2H])NC(=O)c1cc(Oc2ccc(NC(=O)c3nc(SC)oc3-c3ccc(F)s3)cc2F)ccn1] | | 506.1 |
| 36 | 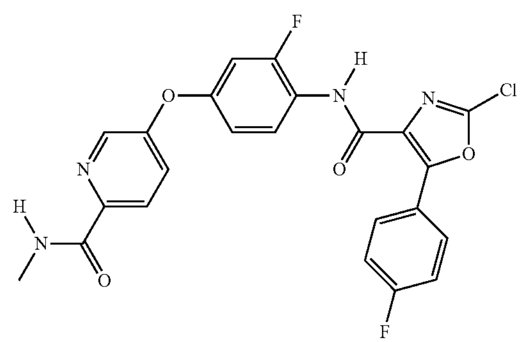 [SMILES: CNC(=O)c1ccc(Oc2ccc(NC(=O)c3nc(Cl)oc3-c3ccc(F)cc3)c(F)c2)cn1] | | 485.1 |
| 37 | 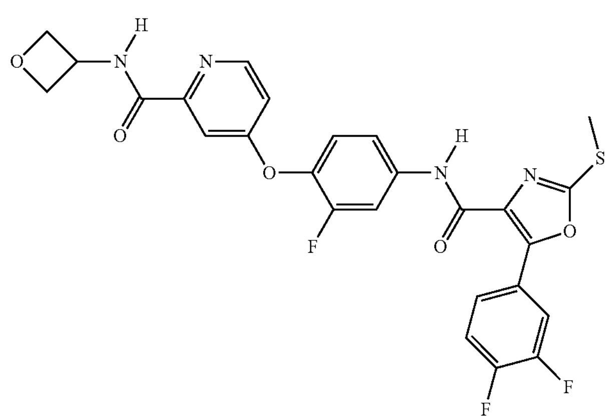 [SMILES: CSc1nc(C(=O)Nc2ccc(Oc3ccnc(C(=O)NC4COC4)c3)c(F)c2)c(-c2ccc(F)c(F)c2)o1] | | 557.2 |

TABLE 1-continued

| Compound Nos. | Structure | ¹H-NMR | Mass Spec. (MZ) |
|---|---|---|---|
| 38 | 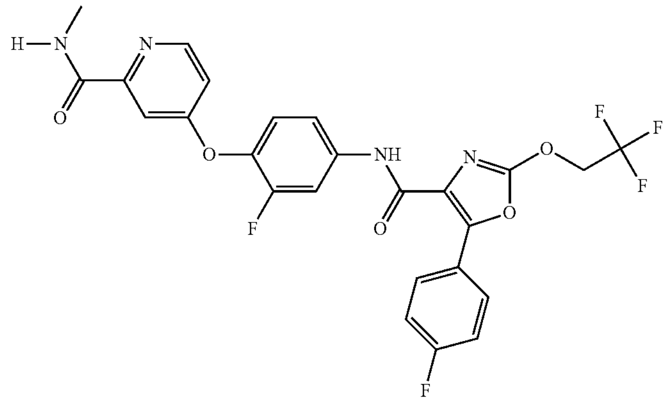 [SMILES: CNC(=O)c1cc(Oc2ccc(NC(=O)c3nc(OCC(F)(F)F)oc3-c3ccc(F)cc3)cc2F)ccn1] | | 549.1 |
| 39 | 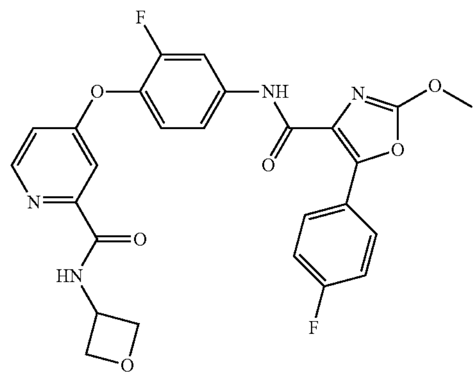 [SMILES: COc1nc(C(=O)Nc2ccc(Oc3ccnc(C(=O)NC4COC4)c3)c(F)c2)c(-c2ccc(F)cc2)o1] | | 523.2 |
| 40 | 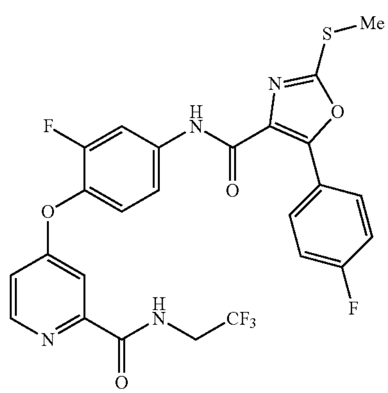 [SMILES: CSc1nc(C(=O)Nc2ccc(Oc3ccnc(C(=O)NCC(F)(F)F)c3)c(F)c2)c(-c2ccc(F)cc2)o1] | | 565.2 |
| 41 | 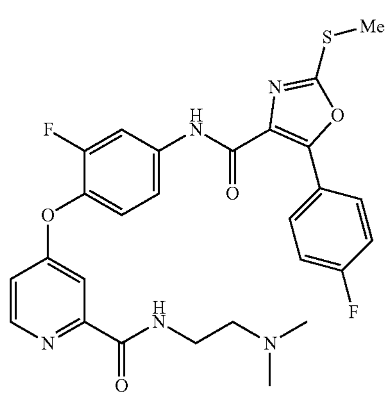 [SMILES: CSc1nc(C(=O)Nc2ccc(Oc3ccnc(C(=O)NCCN(C)C)c3)c(F)c2)c(-c2ccc(F)cc2)o1] | | 554.3 |

TABLE 1-continued

| Compound Nos. | Structure | ¹H-NMR | Mass Spec. (MZ) |
|---|---|---|---|
| 42 | 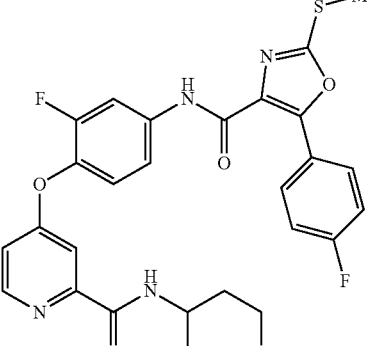 | | 580.2 |
| 43 | 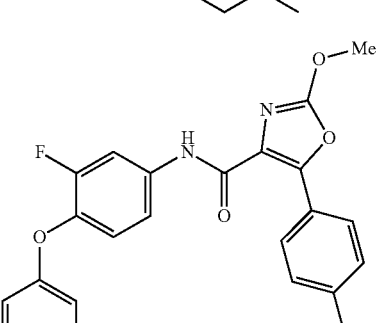 | | 549.1 |

Biochemical Assays

1. Kinase Panel

The disclosed compounds were tested for activity against a panel of 299 kinases. The target enzyme was incubated with fluorescently labeled substrate and test compounds in a standardized reaction mixture in 384 well plates. Upon termination of the reaction, samples were introduced onto microfluidic chips. The samples migrated through channels in the chips and product and substrate were separated based on the difference in their charge (electrophoretic mobility shift). Enzyme activity was measured by direct comparison of the fluorescence in the product and substrate peaks. A selection of kinases from that panel in which one or more of the disclosed compound showed inhibition of kinase activity of 80% or higher is shown below in Tables 2-4. In the tables A=95% or greater at 5 um, B=90%-94% at 5 um, and C=80%-89% at 5 um. [note to draft: we included category D for 50-79 and category E is less than 50%. Feel free to remove if not needed)

TABLE 2

| | Kinase | | | | | | | |
|---|---|---|---|---|---|---|---|---|
| Ex | HIPK4 | TYRO3 | BRK | LCK | EPH-A6 | P38-a | LOK | MER | RIPK2 |
| 1 | B | D | D | E | E | D | E | E | E |
| 2 | A | E | E | E | D | D | D | E | E |
| 3 | A | B | B | A | D | E | E | B | B |
| 4 | A | D | D | C | D | C | D | D | C |
| 5 | B | C | D | D | D | E | E | E | D |
| 6 | B | A | A | A | A | E | E | B | A |
| 7 | B | E | E | A | E | E | C | E | E |
| 8 | A | C | C | C | A | C | D | C | E |
| 9 | A | C | A | A | A | D | A | B | E |
| 10 | A | E | E | E | B | D | E | E | C |
| 11 | A | A | A | B | A | B | B | B | D |
| 12 | B | B | A | A | C | D | D | C | B |
| 13 | A | C | D | B | A | E | E | C | C |
| 14 | A | C | C | D | C | D | C | D | B |
| 15 | A | B | D | D | B | D | C | D | C |
| 16 | A | E | E | E | D | E | D | E | E |
| 17 | A | E | E | E | E | D | E | E |
| 18 | A | E | D | E | D | D | E | E | D |
| 19 | A | D | D | D | C | D | D | D | D |
| 20 | A | D | D | D | D | E | E | E | D |
| 21 | A | E | E | E | D | E | E | E | D |
| 22 | A | B | C | C | D | E | E | C | C |
| 23 | B | C | D | C | C | D | D | D | C |
| 24 | A | D | E | D | D | D | C | E | D |
| 25 | A | D | E | E | D | E | D | E | E |
| 26 | A | B | B | B | B | B | C | C | C |
| 27 | A | E | E | E | E | D | E | E | E |
| 28 | A | E | E | E | E | E | E | E | E |
| 29 | A | D | A | E | C | A | D | D | C |
| 30 | A | A | A | C | A | C | A | C | C |
| 31 | A | D | C | E | C | C | D | E | D |
| 32 | A | B | A | C | B | D | B | C | D |
| 33 | A | D | D | D | D | C | C | E | D |

TABLE 2-continued

| Ex | HIPK4 | TYRO3 | BRK | LCK | EPH-A6 | P38-a | LOK | MER | RIPK2 |
|---|---|---|---|---|---|---|---|---|---|
| 34 | A | C | B | C | B | C | A | B | D |
| 35 | A | D | E | E | D | E | D | E | D |
| 36 | C | E | E | E | D | E | E | E | D |
| 37 | A | E | E | E | E | C | E | E | E |
| 38 | A | D | B | D | C | D | C | C | D |
| 39 | A | D | D | E | C | D | E | E | D |
| 40 | A | E | D | E | E | D | E | E | E |
| 41 | A | D | A | D | C | A | E | D | C |
| 42 | A | E | A | E | D | A | E | E | D |
| 43 | A | E | E | E | E | E | E | E | E |

TABLE 3

| Ex | EPH-A8 | EPH-B2 | PDGFR-b | EPH-B4 | DDR2 | KIT | EPH-A4 | TRKB | P38-b |
|---|---|---|---|---|---|---|---|---|---|
| 1 | E | E | E | E | D | E | E | E | E |
| 2 | D | E | E | E | D | E | D | E | D |
| 3 | D | E | E | E | C | D | E | C | E |
| 4 | D | E | E | E | C | D | E | E | D |
| 5 | D | E | E | E | C | E | E | E | E |
| 6 | C | E | E | E | C | C | E | B | E |
| 7 | E | E | E | E | C | E | E | E | E |
| 8 | B | C | E | D | A | D | B | B | E |
| 9 | A | B | D | B | A | C | B | A | E |
| 10 | D | D | E | D | C | C | B | E | E |
| 11 | C | B | E | C | A | C | B | D | C |
| 12 | D | E | E | D | C | D | D | C | E |
| 13 | C | E | E | D | C | E | D | D | E |
| 14 | D | D | E | D | A | D | D | B | E |
| 15 | C | D | E | D | B | D | D | D | E |
| 16 | E | D | E | E | E | E | E | E | E |
| 17 | E | E | E | E | D | E | E | D | E |
| 18 | E | D | E | E | C | E | E | D | E |
| 19 | D | D | E | D | C | D | D | E | E |
| 20 | D | D | E | E | C | E | E | B | E |
| 21 | D | D | E | E | D | E | E | D | E |
| 22 | E | E | E | E | D | D | E | A | E |
| 23 | D | E | E | D | D | D | D | C | E |
| 24 | D | E | E | E | C | E | E | E | E |
| 25 | E | E | E | E | D | E | E | E | E |
| 26 | C | C | E | C | C | D | C | D | D |
| 27 | E | E | E | E | E | E | E | E | E |
| 28 | E | E | E | E | E | E | E | E | E |
| 29 | D | E | E | E | D | E | D | E | C |
| 30 | B | B | E | C | B | D | B | C | D |
| 31 | E | D | E | D | E | E | E | E | E |
| 32 | C | D | E | D | C | E | D | E | D |
| 33 | E | E | E | E | C | E | E | E | E |
| 34 | C | C | E | C | D | D | B | D | D |
| 35 | E | D | E | E | D | E | E | E | E |
| 36 | E | E | E | E | E | E | E | E | E |
| 37 | E | E | E | E | E | E | E | E | E |
| 38 | D | E | E | D | D | E | E | E | E |
| 39 | E | E | E | E | D | E | E | E | E |
| 40 | E | E | E | E | D | E | E | E | E |
| 41 | D | D | E | E | D | E | D | E | C |
| 42 | E | E | E | E | D | E | E | E | C |
| 43 | E | E | E | E | E | E | E | E | E |

TABLE 4

| Ex | TAOK3 | EPH-A5 | SRC | AXL | TRKA | TIE2 | HIPK3 | TAOK2 | MUSK | PDGFR-a |
|---|---|---|---|---|---|---|---|---|---|---|
| 1 | E | E | E | E | E | E | E | E | E | E |
| 2 | E | D | E | E | E | D | E | E | E | E |
| 3 | E | E | C | C | C | D | E | E | D | D |
| 4 | D | E | E | E | D | E | D | E | E | E |
| 5 | E | E | E | E | E | E | E | E | E | E |
| 6 | E | E | C | C | C | C | E | E | E | E |
| 7 | E | E | E | E | E | E | E | E | E | E |
| 8 | A | C | E | D | B | C | C | C | D | E |

TABLE 4-continued

| Ex | TAOK3 | EPH-A5 | SRC | AXL | TRKA | TIE2 | HIPK3 | TAOK2 | MUSK | PDGFR-a |
|---|---|---|---|---|---|---|---|---|---|---|
| 9 | A | B | D | C | B | B | C | A | D | D |
| 10 | D | D | E | E | D | E | D | E | E | E |
| 11 | E | C | D | B | D | C | E | E | D | B |
| 12 | D | D | D | D | C | D | D | E | D | E |
| 13 | E | D | E | C | D | D | C | E | D | D |
| 14 | B | D | E | E | C | D | D | C | D | E |
| 15 | E | D | E | D | D | E | D | E | E | D |
| 16 | E | E | E | E | E | E | E | E | E | E |
| 17 | E | E | E | E | D | E | E | E | E | E |
| 18 | E | E | E | E | D | E | E | E | E | E |
| 19 | D | D | E | E | D | D | E | E | E | D |
| 20 | D | D | E | E | C | D | D | E | D | E |
| 21 | D | D | E | E | D | D | D | E | E | E |
| 22 | D | E | E | C | B | B | D | D | D | D |
| 23 | D | D | E | D | C | D | E | D | E | E |
| 24 | E | E | E | E | D | E | D | E | E | E |
| 25 | E | E | E | E | E | E | E | E | E | E |
| 26 | C | C | D | D | C | C | D | D | C | D |
| 27 | E | E | E | E | E | E | E | E | E | E |
| 28 | E | E | E | E | E | E | E | E | E | E |
| 29 | D | E | E | D | E | E | C | D | E | E |
| 30 | C | C | D | D | B | C | B | D | C | D |
| 31 | E | E | E | E | E | E | E | E | E | E |
| 32 | D | D | D | C | D | D | D | D | E | E |
| 33 | D | E | E | E | D | E | D | E | E | E |
| 34 | C | C | C | D | C | C | E | D | E | E |
| 35 | E | E | E | E | E | E | E | E | E | E |
| 36 | E | E | E | E | E | E | D | E | E | E |
| 37 | E | E | E | E | E | E | E | E | E | E |
| 38 | E | E | D | C | D | D | D | E | E | E |
| 39 | E | E | E | E | E | E | E | E | E | E |
| 40 | E | E | E | E | E | E | E | E | E | E |
| 41 | D | D | E | E | E | E | E | E | E | E |
| 42 | E | E | E | E | E | E | D | E | E | E |
| 43 | E | E | E | E | E | E | E | E | E | E |

While we have described a number of embodiments, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. A compound selected from:

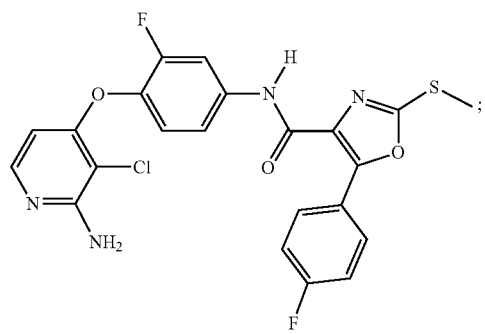

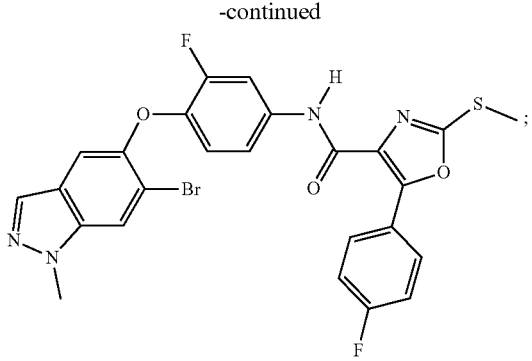

-continued

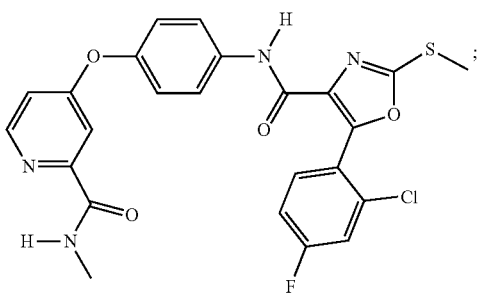

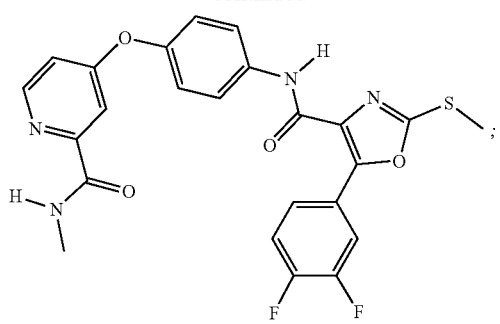
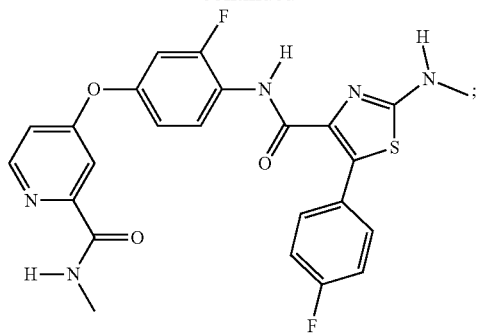
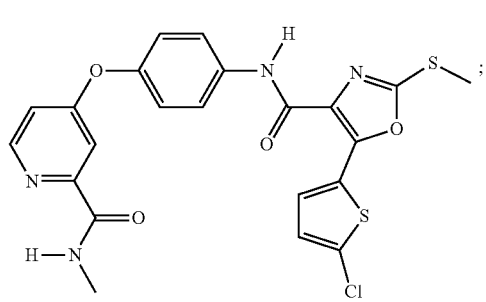
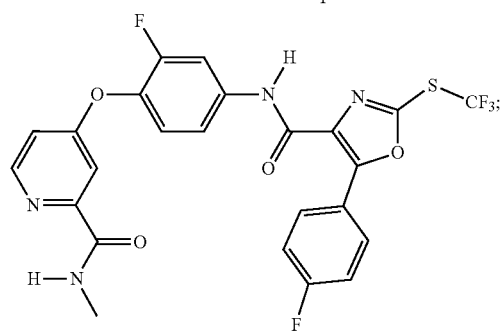
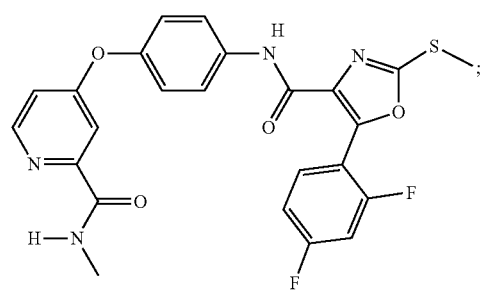
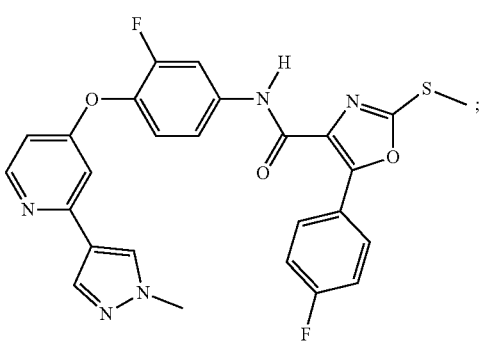
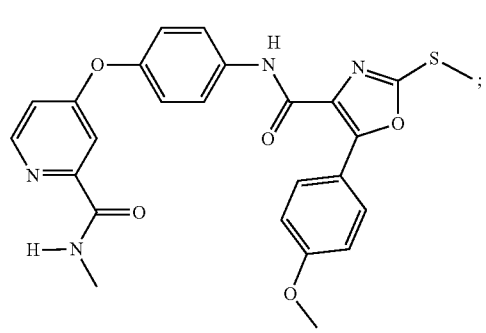
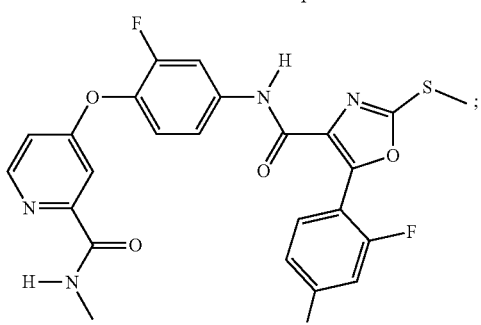
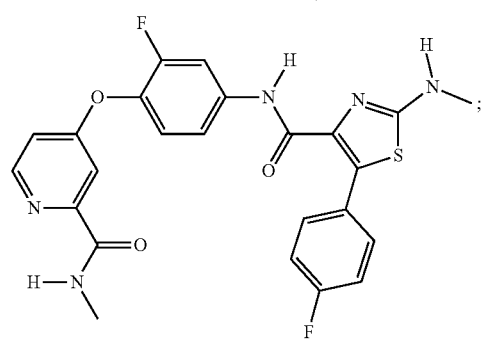
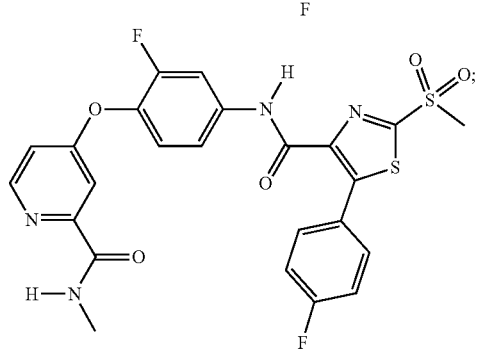

43
-continued
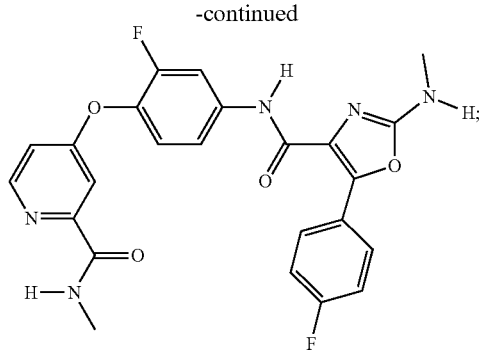
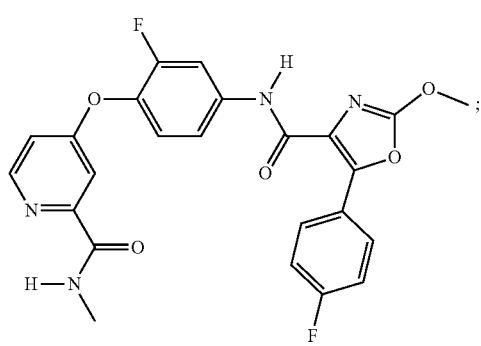
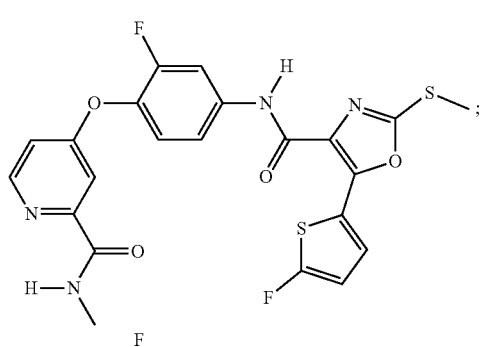
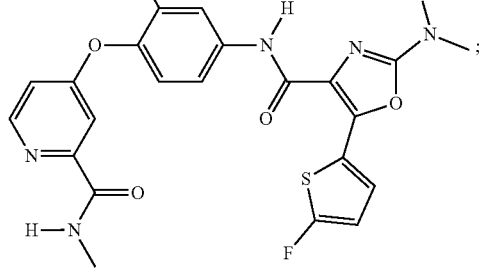
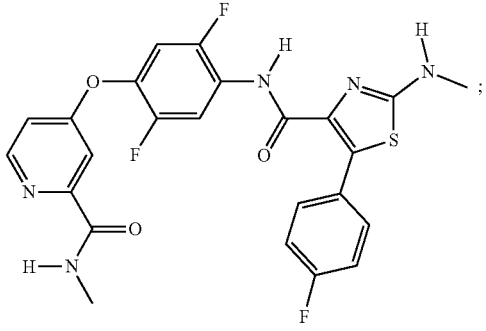
44
-continued
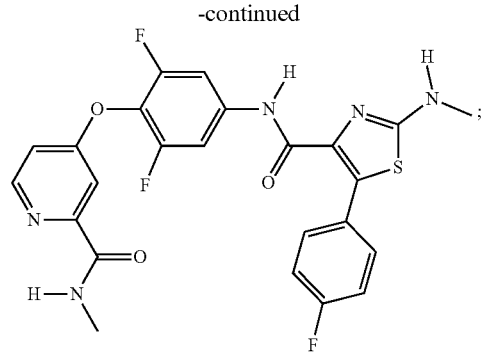
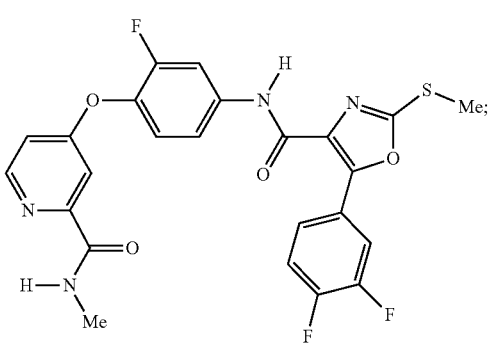
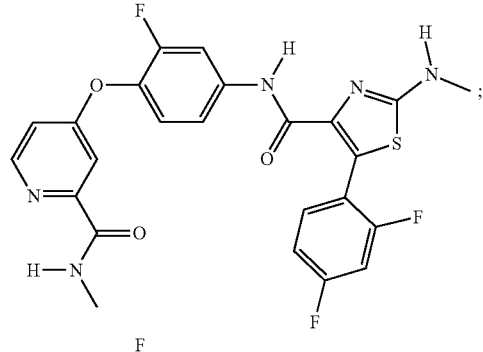
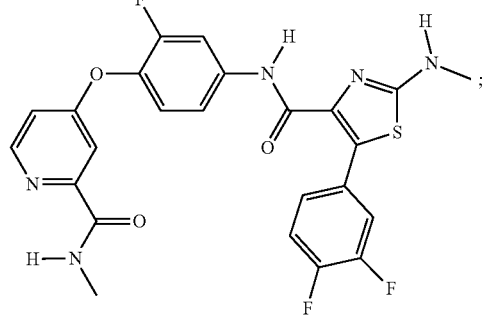
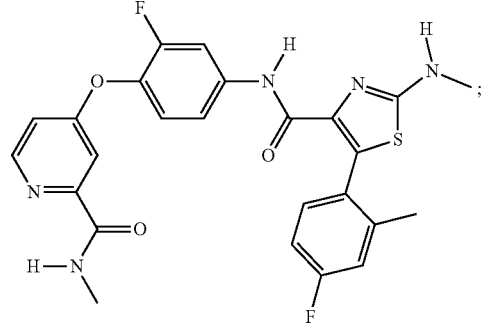

45
-continued
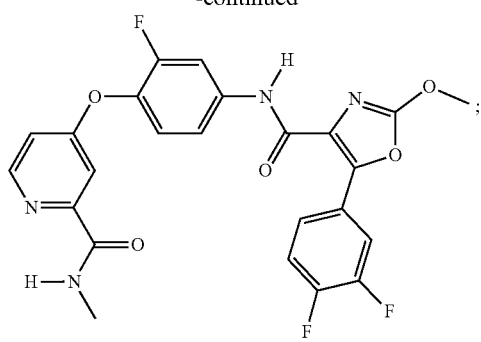
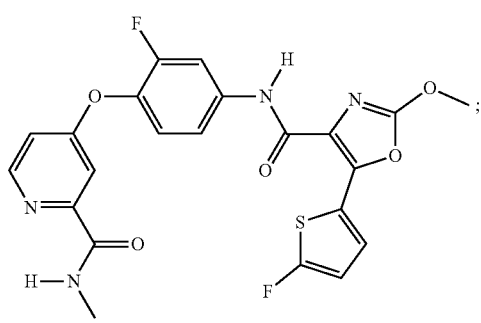
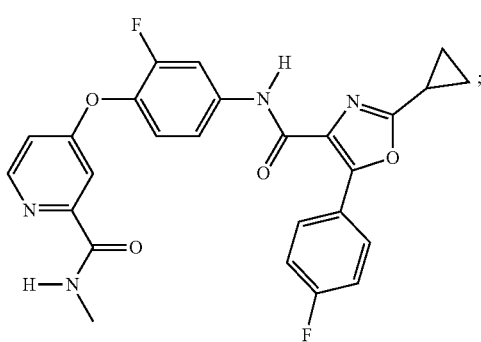
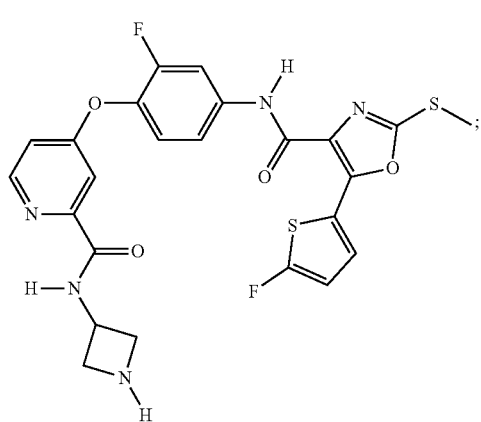
46
-continued
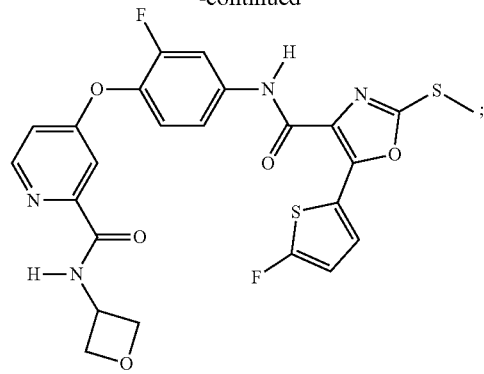
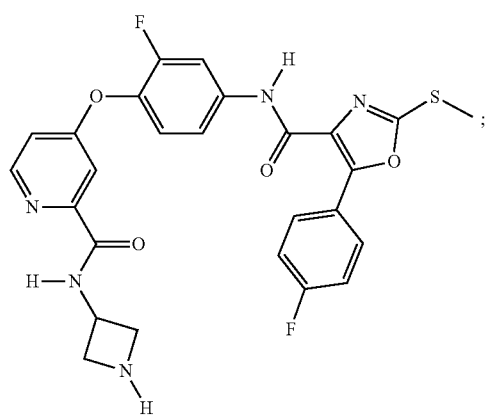
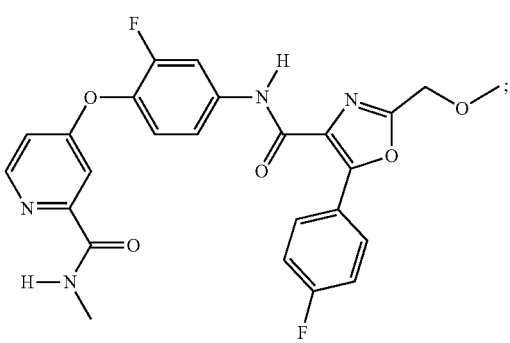
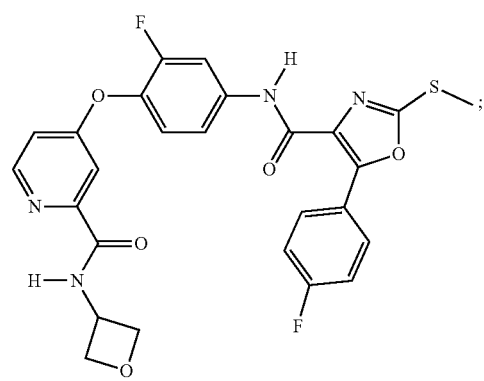

47
-continued
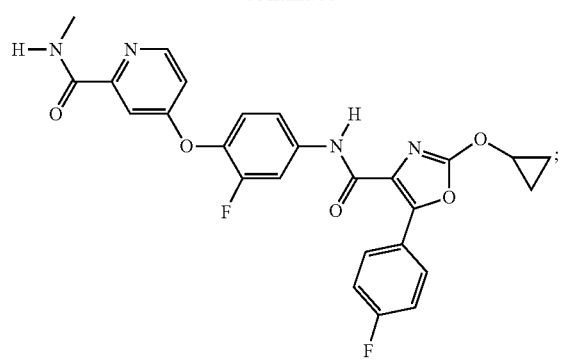
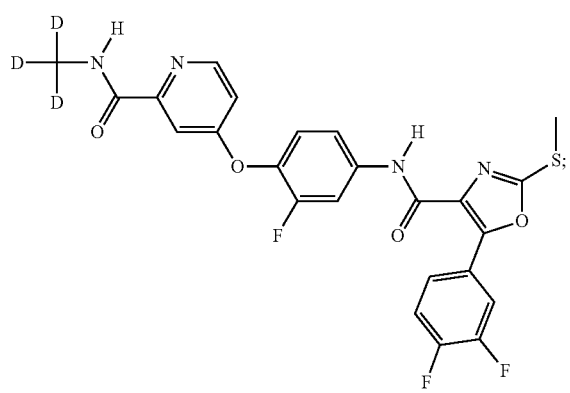
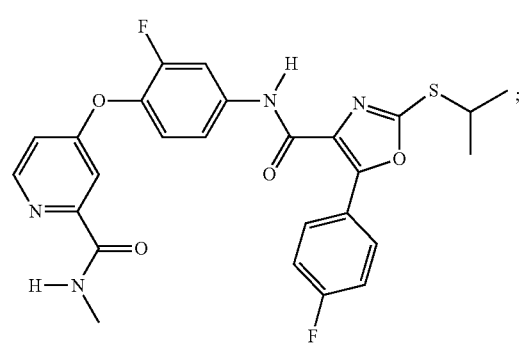
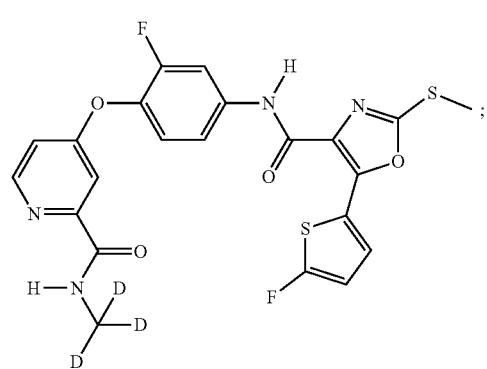
48
-continued
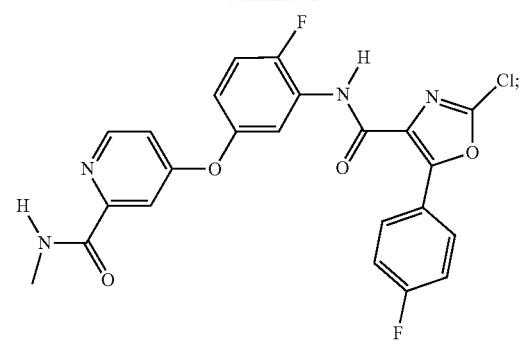 [SMILES: CNC(=O)c1cc(Oc2ccc(F)c(NC(=O)c3nc(Cl)oc3-c3ccc(F)cc3)c2)ccn1]
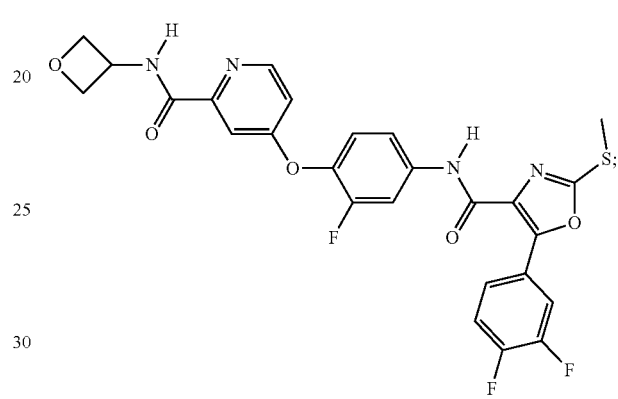
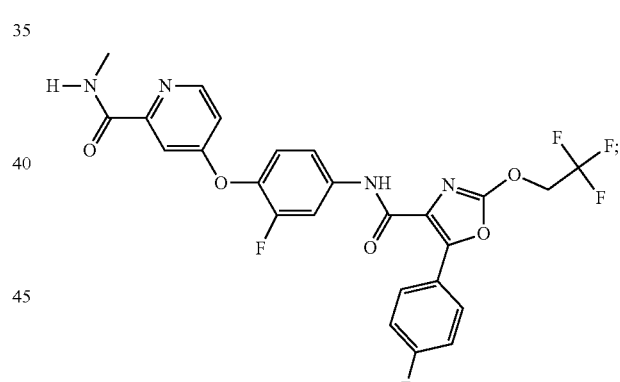
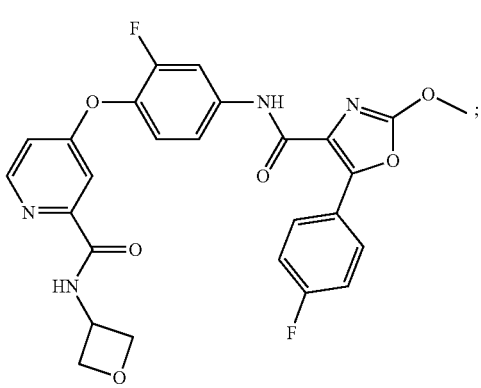

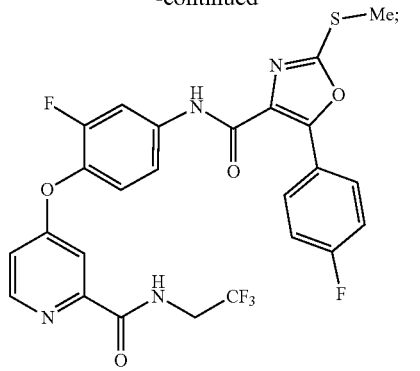

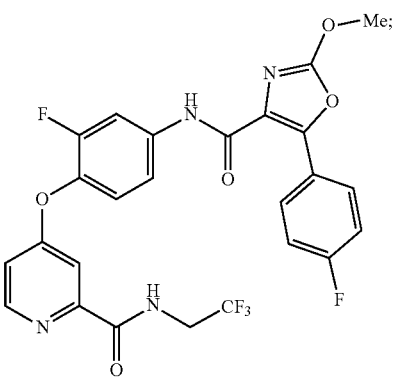

or a pharmaceutically acceptable salt thereof of any of the foregoing.

2. A pharmaceutical composition comprising a compound of claim 1, or a pharmaceutically acceptable salt thereof; and a pharmaceutically acceptable carrier.

3. A method of treating prostate cancer, lung cancer, pancreatic cancer, bladder cancer, colon cancer, diffuse large B-cell lymphoma, rectal cancers, melanoma, stomach cancer, esophageal cancer, or uterine cancer in a subject, comprising administering to the subject, a therapeutically effective amount of a compound of claim 1, or a pharmaceutically acceptable salt thereof, or the composition of claim 2.

4. A method of, comprising administering to a male subject, a therapeutically effective amount of a compound of claim 1, or a pharmaceutically acceptable salt thereof, or the composition of claim 2.

* * * * *